(12) United States Patent
von Segesser

(10) Patent No.: US 7,967,776 B2
(45) Date of Patent: Jun. 28, 2011

(54) HIGH PERFORMANCE CANNULAS

(75) Inventor: Ludwig K. von Segesser, Lausanne (CH)

(73) Assignee: Coraflo, Ltd, Lausanne (CH)

( * ) Notice: Subject to any disclaimer, the term of this patent is extended or adjusted under 35 U.S.C. 154(b) by 231 days.

(21) Appl. No.: 10/886,983

(22) Filed: Jul. 7, 2004

(65) Prior Publication Data
US 2005/0038408 A1 Feb. 17, 2005

Related U.S. Application Data

(60) Provisional application No. 60/484,673, filed on Jul. 7, 2003.

(51) Int. Cl.
*A61M 25/00* (2006.01)
(52) U.S. Cl. ............ 604/28; 604/104; 604/509
(58) Field of Classification Search ........... 604/104, 604/264, 164.01, 523, 284, 506, 507, 509, 604/28, 43
See application file for complete search history.

(56) References Cited

U.S. PATENT DOCUMENTS

| | | | | |
|---|---|---|---|---|
| 4,406,656 A | * | 9/1983 | Hattler et al. | 604/523 |
| 5,067,491 A | | 11/1991 | Taylor, II et al. | 128/748 |
| 5,460,170 A | * | 10/1995 | Hammerslag | 600/201 |
| 5,573,509 A | | 11/1996 | Thornton | 604/102 |
| 5,674,240 A | | 10/1997 | Bonutti et al. | 606/198 |
| 5,795,289 A | | 8/1998 | Wyttenbach | 600/207 |
| 5,814,058 A | * | 9/1998 | Carlson et al. | 606/185 |
| 5,817,071 A | | 10/1998 | Dewindt et al. | 604/264 |
| 5,827,319 A | | 10/1998 | Carlson et al. | 606/191 |
| 5,911,702 A | | 6/1999 | Romley et al. | 604/53 |
| 5,976,114 A | | 11/1999 | Jonkman et al. | 604/264 |
| 5,976,119 A | * | 11/1999 | Spears et al. | 604/508 |
| 6,036,711 A | | 3/2000 | Mozdzierz et al. | 606/185 |

(Continued)

FOREIGN PATENT DOCUMENTS

EP 0 839 549 A1 5/1998

(Continued)

OTHER PUBLICATIONS

Jegger et al. *Perfusion*, 00:1-4 (2003).

(Continued)

*Primary Examiner* — Nicholas D Lucchesi
*Assistant Examiner* — Laura A Bouchelle
(74) *Attorney, Agent, or Firm* — Mintz Levin Cohn Ferris Glovsky and Popeo PC

(57) ABSTRACT

A cannula having a proximal end, a distal end, and a lumen extending between the proximal and distal ends is provided. The diameter of the lumen of the cannula can be varied to take into account differences in the diameter of access and target vessels during cannulation. The cannula is further characterized by at least one mechanism that, upon actuation, serves to alter the conformation of the cannula between a normal profile conformation and a low profile conformation. The normal profile conformation is characterized by the cannula having a lumen diameter at the point of insertion, which is smaller than the lumen diameter both proximal and distal to the point of insertion, with the lumen diameter distal to the point of insertion also expandable to the diameter of the cannulated vessel of the patient. The low profile conformation is characterized by the cannula having a lumen diameter at the point of insertion that is greater than the lumen diameter distal to the point of insertion.

12 Claims, 14 Drawing Sheets

U.S. PATENT DOCUMENTS

| | | | | |
|---|---|---|---|---|
| 6,102,894 | A | 8/2000 | Dysarz | 604/110 |
| 6,231,544 | B1 * | 5/2001 | Tsugita et al. | 604/104 |
| 6,358,266 | B1 * | 3/2002 | Bonutti | 606/190 |
| 6,626,859 | B2 | 9/2003 | von Segesser | 604/28 |
| 6,673,042 | B1 * | 1/2004 | Samson et al. | 604/104 |
| 6,709,428 | B2 * | 3/2004 | Sagstetter | 604/523 |
| 2002/0010440 | A1 * | 1/2002 | von Segesser | 604/272 |
| 6,072,154 | A | 6/2000 | Maynard | 219/209 |
| 6,096,012 | A | 8/2000 | Bogert et al. | 604/264 |

FOREIGN PATENT DOCUMENTS

| | | |
|---|---|---|
| WO | WO 98/19730 | 5/1998 |
| WO | WO 99/15226 | 4/1999 |

OTHER PUBLICATIONS

Mueller et al. *Interact. Cardiovasc. Thorac. Surg.*, 1:23-27 (2002).
International Search Report for PCT/IB2004/002672, mailed Dec. 3, 2004.

* cited by examiner

LOCKED

UNLOCKED

HIGH PERFORMANCE CANNULAS

RELATED APPLICATIONS

This application claims priority to U.S. Provisional Patent Application Ser. No. 60/484,673, filed Jul. 7, 2003, which is herein incorporated by reference in its entirety.

FIELD OF THE INVENTION

The invention relates to cannulas and, more particularly, to high performance cannulas, where the diameter of the lumen of the cannula can be varied.

BACKGROUND OF THE INVENTION

Cannulas are used in a wide variety of applications. For example, cannula assemblies are typically used in minimally invasive surgical procedures including laparoscopic, endoscopic, and arthroscopic procedures. Cannulas can also be used to deploy operating instrumentation during such minimally invasive procedures. Additionally, during coronary surgery, venous and arterial cannulas are used to conduct blood between the body and the bypass equipment. Moreover, cannulas are also used as vents, as sumps, and for chest tube fluid suction. Cannulas can also be used in a variety of non-medical contexts.

SUMMARY OF THE INVENTION

In one aspect, the invention relates to a cannula adapted for insertion at a point of insertion. The cannula includes a cannula body having a proximal end, a distal end, and a lumen extending between the proximal and distal ends. The lumen has a diameter and the cannula body includes a plurality of flexible filaments that allow the diameter of the lumen to be varied. The distal end optionally further comprises a tip, which can be removable or eccentrically located. The cannula also includes at least one mechanism that, upon actuation, serves to alter the conformation of the cannula between a normal profile conformation and a low profile conformation. For example, the mechanism is selected from a mandrel, an electric motor, a change in pressurization, a wrapping string, a balloon and a sheath. When the cannula is in use, the normal profile conformation is characterized by the cannula having a lumen diameter at the point of insertion, which is smaller than the lumen diameter both proximal and distal to the point of insertion. The lumen diameter distal to the point of insertion is expandable up to the diameter of a surrounding vessel or up to the maximum lumen diameter. The low profile conformation is characterized by the cannula having a lumen diameter at the point of insertion that is greater than the lumen diameter distal to the point of insertion.

The plurality of flexible filaments may include one or more materials selected from metals, shape-memory metals, alloys, plastics, textile fibers, synthetic fibers, and/or combinations thereof. For example, the metal can be stainless steel. Moreover, the plurality of flexible filaments can have a shape selected from round, oval, flattened, triangular, rectangular and combinations thereof. In one embodiment, the plurality of flexible filaments are textile fibers.

Those skilled in the art will recognize that the plurality of flexible filaments can be braided together, knitted together or interwoven. Alternatively, the plurality of flexible filaments are interlaced.

The cannula is designed to be inserted into hollow organ, which can be selected from, for example, a vein, an artery, a urethra, a ureter, an intestine, an esophagus, a trachea, a bronchial tube, a pleural space, and/or a peritoneum.

When the cannula is in its normal profile conformation when in use, the lumen diameter distal to the point of insertion varies in relation to the diameter of the surrounding vessel. Further, the cannula is in its normal profile conformation when in use, the portion of the cannula distal to the point of insertion supports an inner surface of the surrounding vessel.

The plurality of flexible filaments may be elastic and/or plastic in nature. The cannula may be coated with a watertight coating, which can be a plastic, such as, for example, silicone. The cannula tip may be potted using a material such as a photoactivated epoxy. The cannula may further include a connecting sleeve to couple the cannula to a device.

The flow rate of fluid through the cannulas of the invention can be less than about 150 mL/min. In some of the cannulas, the flow rate of fluid through the cannula is between about 1 mL/min and about 10 mL/min.

The invention provides methods for using the cannula in medical contexts. Such methods include placing the cannula in its low profile conformation, inserting the cannula into a hollow organ of a patient at a point of insertion, and returning the cannula to its normal profile conformation. In the normal profile conformation, the cannula expands distal to the point of insertion up to the diameter of the hollow organ or up to the maximum diameter of the lumen.

For example, when the cannula is in the normal profile conformation, the diameter of the cannula distal to the point of insertion varies in relation to the diameter of the hollow organ. Inserting the cannula into the hollow organ of the patient can include inserting the cannula into a location selected from the peritoneum, the trachea, the chest, the cardiovascular system, the kidneys, and the urinary system. For example, the hollow organ can be selected from a vein, an artery, a urethra, a ureter, an intestine, an esophagus, a trachea, a bronchial tube, a pleural space, and a peritoneum. In one specific embodiment, the cannula is inserted into the trachea, and the cannula can be inserted transorally, transnasally, or through a tracheotomy.

When the cannula is used during cardiac surgery, the cannula may have a flow rate of fluid through the cannula of between about 100 mL/min and 6 L/min. When used during dialysis or hemofiltration, the cannula may have a flow rate of fluid through the cannula between about 100 mL/min and 500 mL/min. When used for the intravenous delivery of fluids, the cannula may have a flow rate between about 1 mL/min and about 10 mL/min.

The invention also provides methods for using the cannula in non-medical contexts. Such methods include placing the cannula in its low profile conformation; inserting the cannula into an object to be cannulated selected from the group consisting of tubing, a container, a fluid-filled container, a powder-filled container, and a gas-filled container; and returning the cannula to its normal profile conformation. In the normal profile conformation, the cannula expands distal to the point of insertion up to the diameter of the object or up to the maximum lumen diameter.

Also provided are dual lumen cannula adapted for insertion at a point of insertion for use in, for example, peritoneal dialysis, hemodialysis or hemofiltration. Such dual lumen cannulas include a first cannula body having a proximal end, a distal end, and a lumen extending between the proximal and distal ends, and a second cannula body having a proximal end, a distal end, and a lumen extending between the proximal and distal ends, the lumen of the first and second cannula bodies having a diameter. The first and second cannula bodies each include a plurality of flexible filaments that allow the diameter of the first and second lumen to be varied. The first and second distal ends may optionally further include a tip, which is removable or eccentrically located. The dual lumen cannula includes at least one mechanism that, upon actuation, serves to alter the conformation of the first cannula body, the second cannula body, or both the first cannula body and the second cannula body, between a normal profile conformation and a low profile conformation.

When the dual lumen cannula is in use, the normal profile conformation is characterized by the first and second cannula bodies having a lumen diameter at the point of insertion, which is smaller than the lumen diameter both proximal and distal to the point of insertion. The lumen diameters of the first and second cannula bodies distal to the point of insertion are expandable up to the diameter of a surrounding vessel or up to the maximum lumen diameter. The low profile conformation is characterized by the first and second cannula bodies having a lumen diameter at the point of insertion that is greater than the lumen diameter distal to the point of insertion.

The flexible filaments that make up the cannula body of the dual lumen cannula may include one or more materials selected from metals, shape-memory metals, alloys, plastics, textile fibers, synthetic fibers, and/or combinations thereof. Moreover, the at least one mechanism is selected from a mandrel, an electric motor, a change in pressurization, a wrapping string, a balloon and/or a sheath. The first and second cannula bodies of the dual lumen cannula can be positioned coaxially or adjacently.

The invention also provides methods for manufacturing the cannula according to the invention. For example, the cannula can be made by injection molding, laser-cutting, water-cutting, extrusion and combinations thereof.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

DETAILED DESCRIPTION OF THE INVENTION

High Performance Cannulas

Figure 1A:
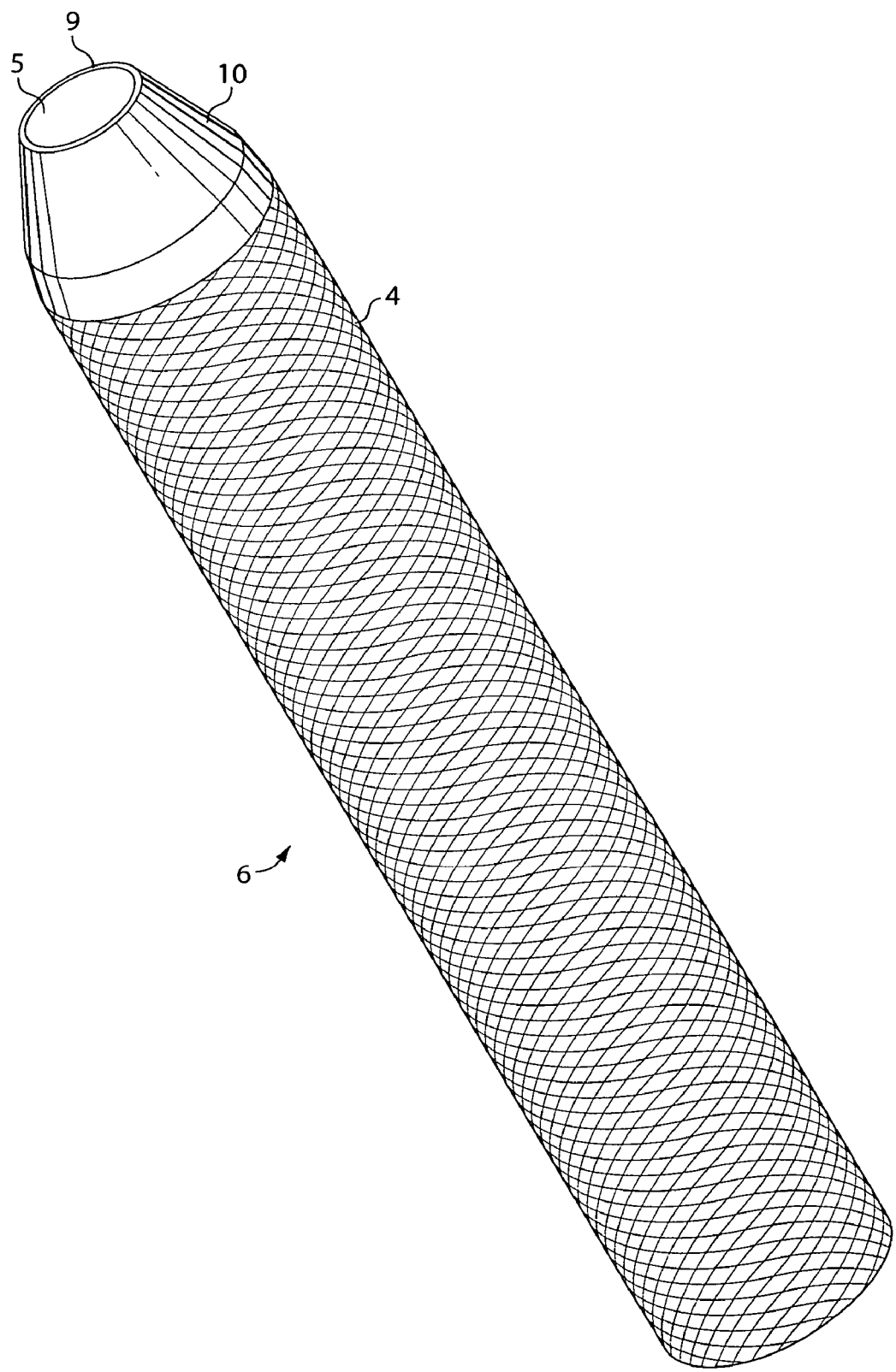
FIG. 1A illustrates a cannula according to one embodiment of the invention in its normal profile conformation. Cannulas according to this embodiment can be used, for example, in open heart and open chest surgical procedures.
Figure 1B:
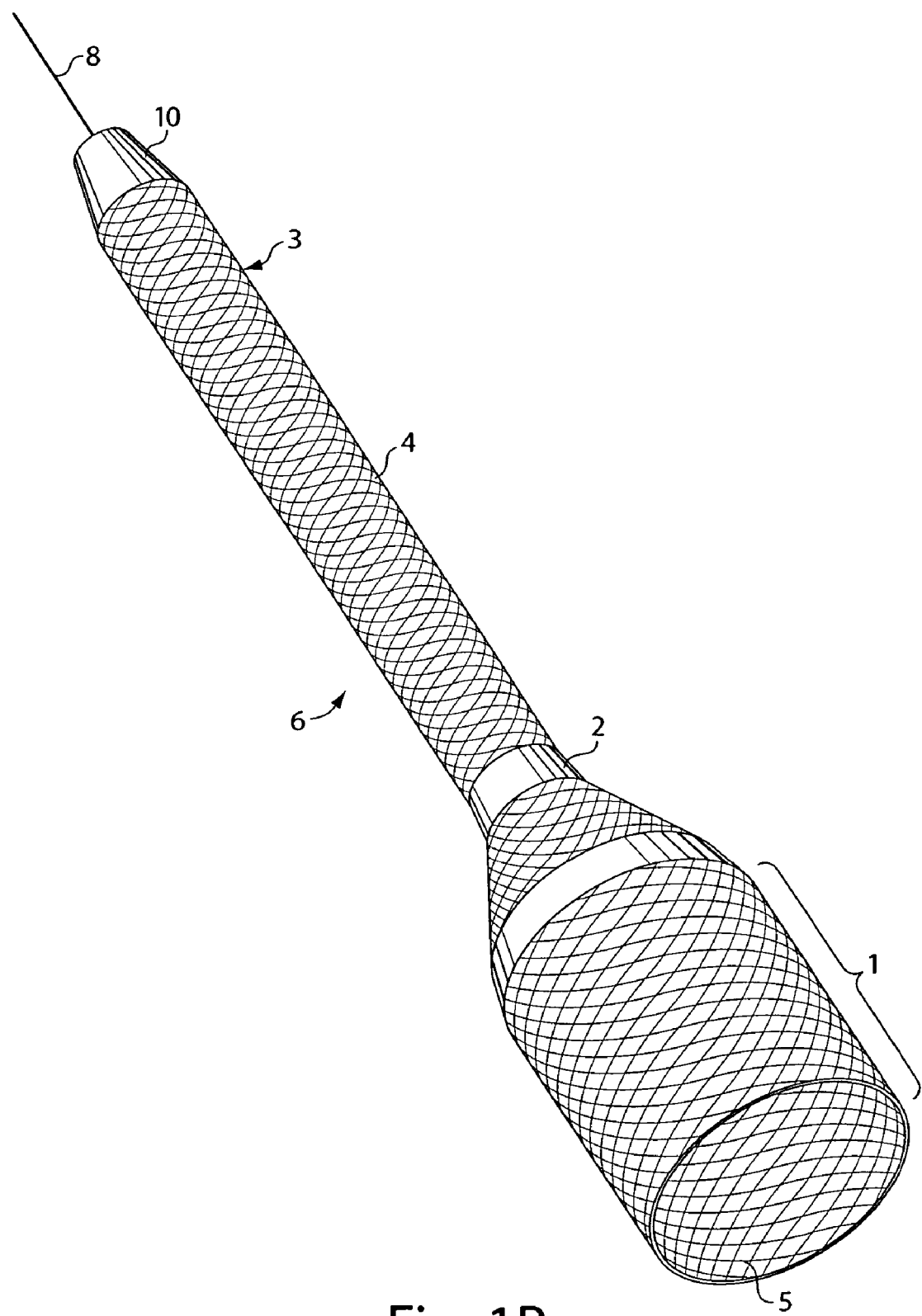
FIG. 1B illustrates a cannula according to one embodiment of the invention in its low profile conformation.

Minimally invasive open-heart surgery presents new problems and challenges, some of which are due to the inadequate design of traditional cannulas. In such cannulas, the external diameter of cannulas to be used in target blood vessels is determined by the internal diameter of the access vessel, which is usually smaller than that of the target vessel. For example, in peripheral cannulation, the diameter of the access vessel (e.g. the femoral vein) is significantly smaller than the diameter of the target vessel (e.g. the vena cava). As a result of this difference in diameters, relatively high cannula gradients can occur. Therefore, during peripheral cannulation, venous return is poor and must be augmented with vacuums or pumps. Moreover, during minimally invasive open-heart surgery, the tip of the venous cannulas cannot be placed in the right atrium of the heart, which is open by definition. Thus, it can be impossible to reach target flow rates despite this augmentation of the venous return, because the floppy caval veins collapse and obstruct the orifices of the cannula. While previous cannulas have provided expandable scaffolding, the expandable scaffolding of those cannulas acts to provide support for the surrounding vasculature and do not allow the luminal diameter of the cannula to be varied. See, e.g., U.S. Pat. No. 6,673,042.

Those skilled in the art will recognize that a short segment of a tube or vessel having a narrow internal diameter will not impede flow through the tube or vessel. In contrast, a long portion of a tube or vessel having a small or narrow diameter will impede flow through the object.
Specifically, the segment having narrow internal diameter may constitute between 0% and 50% of the total length of the object. The skilled artisan will also recognize that, in a clinical setting, coronary artery stenoses of less than 50% of the diameter of the artery are not considered significant, and, thus, are not operated on. By "coronary artery stenoses" is meant any stricture or narrowing of a coronary artery.

Based on these principles and observations, a cannula having a narrow diameter only where absolutely necessary would be expected to have much better flow rate characteristics than a cannula having a narrow diameter over most of its length. Thus, the cannulas according to the present invention may have a small diameter only at the point of insertion. Preferably, the narrow diameter of the cannula occurs over less than 50% of the total length of the cannula, more preferably, less than 40%, more preferably less than 30%, more preferably less than 20%, and most preferably, less than 10%. By "point of insertion" is meant the location where the cannula is inserted into the object to be cannulated. Examples of suitable points of insertion include, but are not limited to, arterial walls; venous walls; the skin; an orifice; the exterior of tubes and containers; and a fixed aperture on a tank or container.

Because of the narrow diameter of the cannula at the point of insertion, the access aperture of the cannula will be small. By "access aperture" is meant the hole that allows the cannula to access the object or vessel to be cannulated, i.e., the hole at the point of insertion.

Those skilled in the relevant arts will recognize that cannulation is not limited to medical contexts. For example, non-medical uses for the high performance cannulas of the invention include, but are not limited to, any situation where a continuous fluid flow and a small access aperture is desired. Examples of non-medical uses of the high performance cannulas according to the invention include, but are not limited to, methods for repairing ruptured pipe, hose, or tubing where a continuous fluid flow and a small access aperture are needed without having to replace the entire length of ruptured pipe, hose, or tubing. Other examples of non-medical uses include filling or draining liquids or liquid-like materials from any reservoir, such as a tank, pipe or cavern.

Likewise, the cannulas according to the invention can be used as previously described in the art. For example, see U.S. Pat. Nos. 6,102,894; 6,096,012; 6,072,154; 6,036,711; 5,976,114; and 5,817,071, each of which is incorporated herein by reference.

When used in a medical context, the cannulas according to this invention can take advantage of the geometry of an individual's vascular tree. Specifically, cannulas according to this invention are able to compensate for the differences in diameter between access vessels (typically smaller in diameter) and target vessels (typically larger in diameter). To compensate for these differences in diameter, the diameter of the lumen of the high performance cannula is adjustable before, during and after cannulation (i.e., insertion). Specifically, after cannulation the diameter of the cannula either expands to that of the surrounding vessel or environment or returns to its normal profile conformation. In contrast, traditional cannulas are limited by the diameter of the access vessel.

Cannulas according to the invention can include a cannula body having a proximal end, a distal end, and a lumen extending between the proximal and distal ends. The lumen has a diameter, and the cannula is made of a flexible material that allows the diameter of the lumen to be varied. Such cannulas also include means for altering the conformation of the cannula between a normal profile conformation and a low profile conformation, wherein the normal profile conformation is characterized by the cannula having a lumen diameter at the point of insertion and wherein the low profile conformation is characterized by the cannula having a lumen diameter at the point of insertion that is greater than the lumen diameter distal to the point of insertion. Following cannulation, the lumen diameter distal to the point of insertion is expandable to the diameter of the cannulated vessel or to the normal profile conformation diameter of the lumen.

Figure 2A:
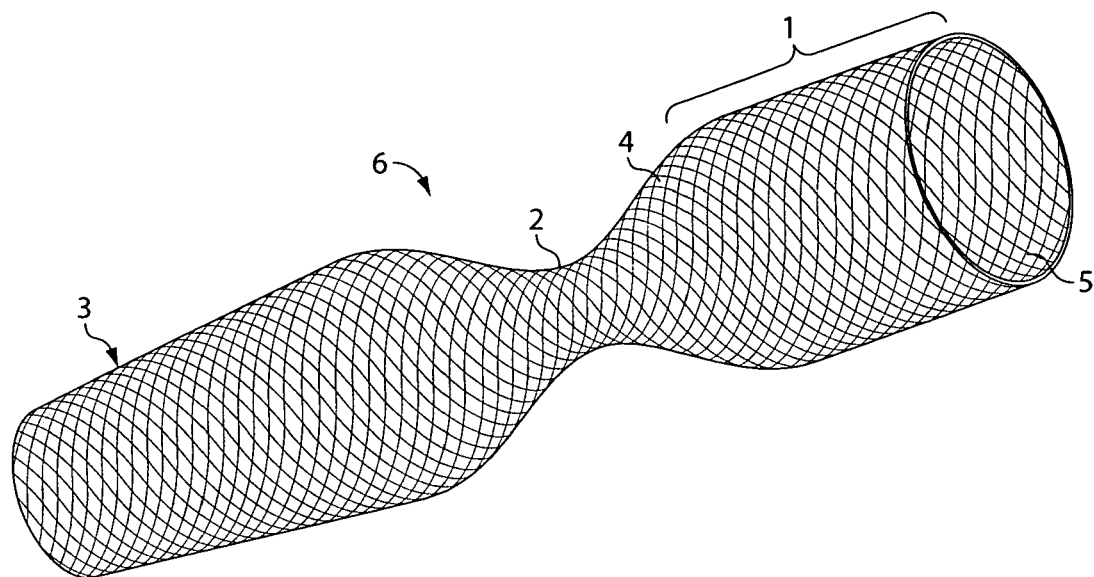
FIG. 2A is a perspective view showing a view of a cannula according to one embodiment of the invention in a normal profile conformation when the cannula is in use according to the methods of the invention.

The diameter of the lumen can be varied by altering the cannula between a low profile conformation and a normal profile conformation. By "normal profile conformation" is meant any conformation similar to that shown in FIG. 1A or 2A. According to one embodiment, and as illustrated in FIG. 2A, for example, when the cannula 6 is in use, the normal profile conformation may be characterized by the cannula 6 having a lumen diameter 5 at the point of insertion 2, which is smaller than the lumen diameter 5 both proximal and distal to the point of insertion 2 (e.g., the diameter of the surrounding vessel). Alternatively, as shown in FIG. 1A, the cannula 6 in a normal profile conformation following cannulation can have the shape and diameter of the lumen 5 of the cannula 6 prior to cannulation. In either normal profile conformation, the cannula 6 is characterized by a larger diameter of the lumen 5 as compared to the diameter of the lumen 5 when the cannula is in the low profile conformation.

Figure 2B:
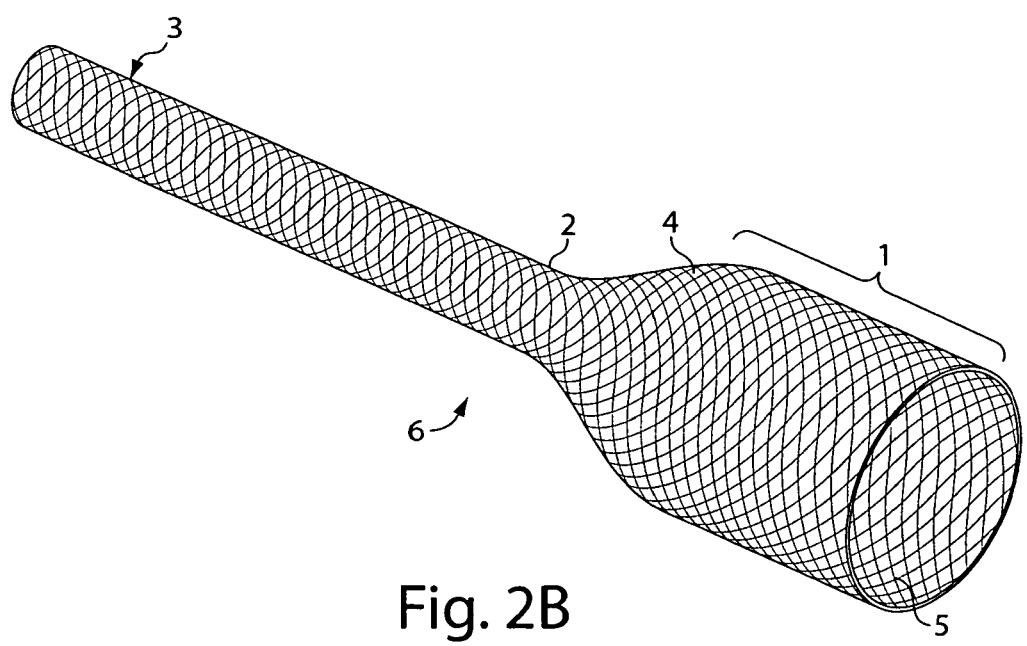
FIG. 2B is a perspective view showing a view of a cannula according to one embodiment of the invention in a low profile conformation.
Figure 3A:
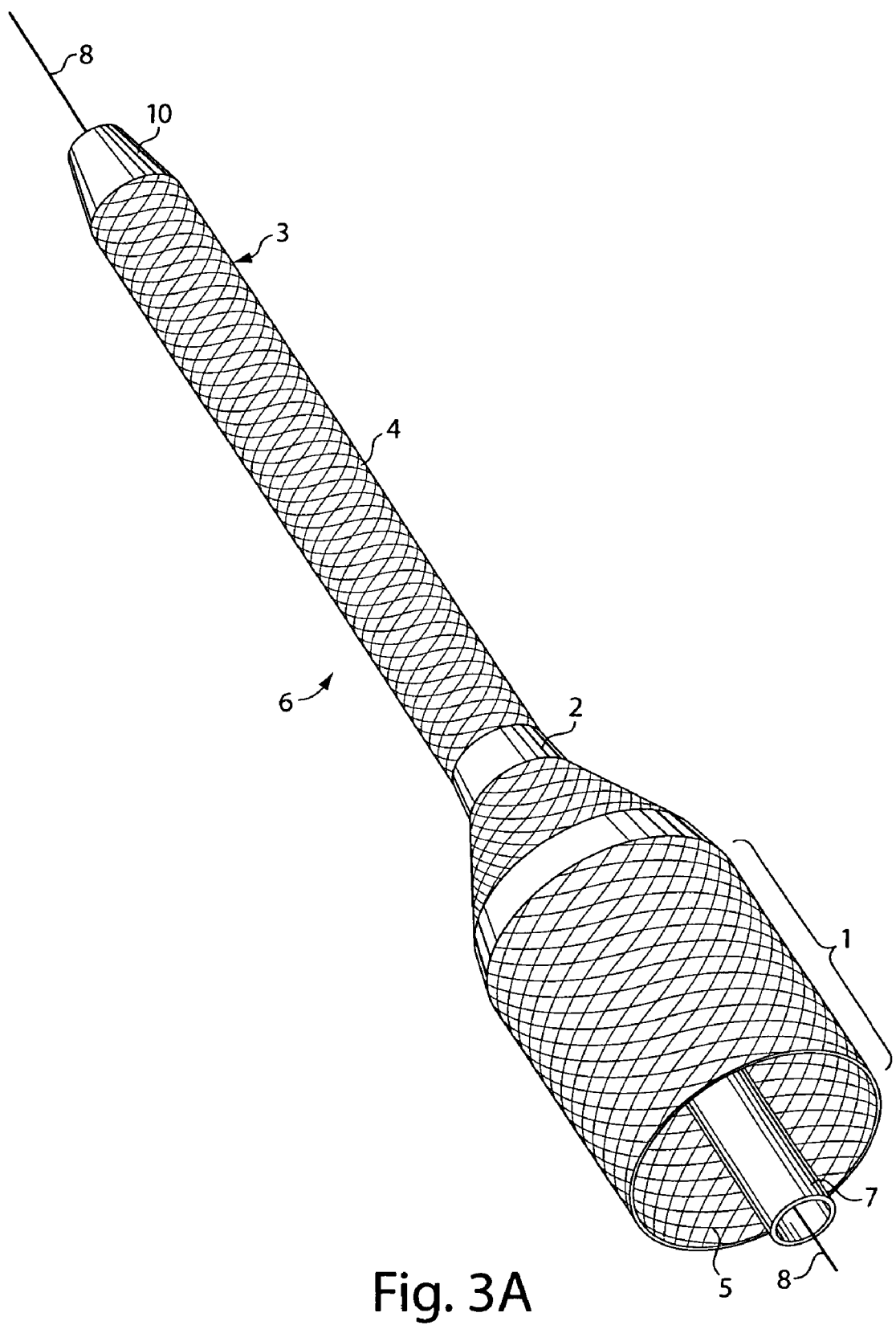
FIG. 3A is a computer-generated drawing showing the high performance cannula according to one embodiment of the invention stretched on a mandrel.
Figure 3B:
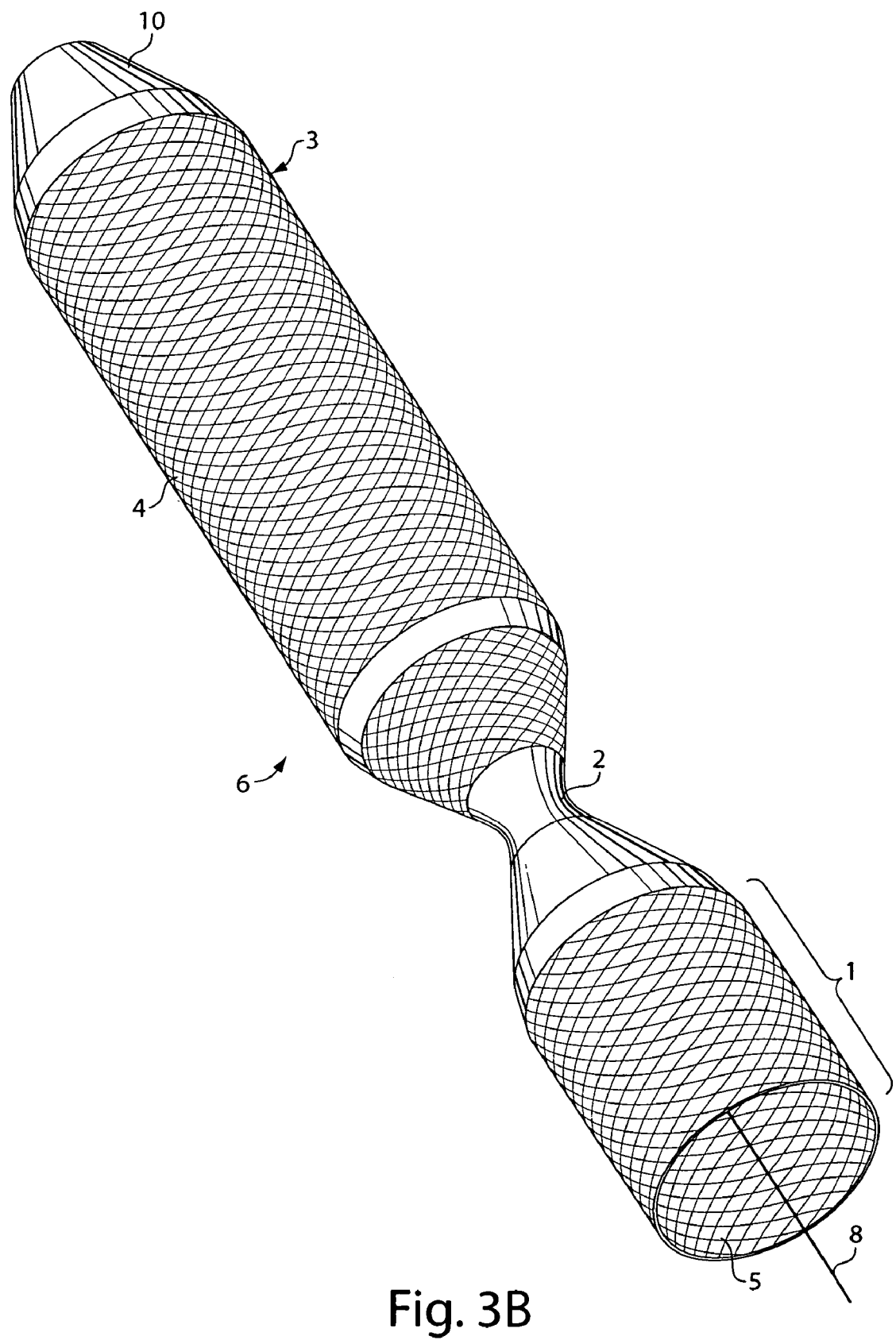
FIG. 3B is a computer-generated drawing showing the high performance cannula according to one embodiment of the invention after removal of the mandrel.
Figure 4:
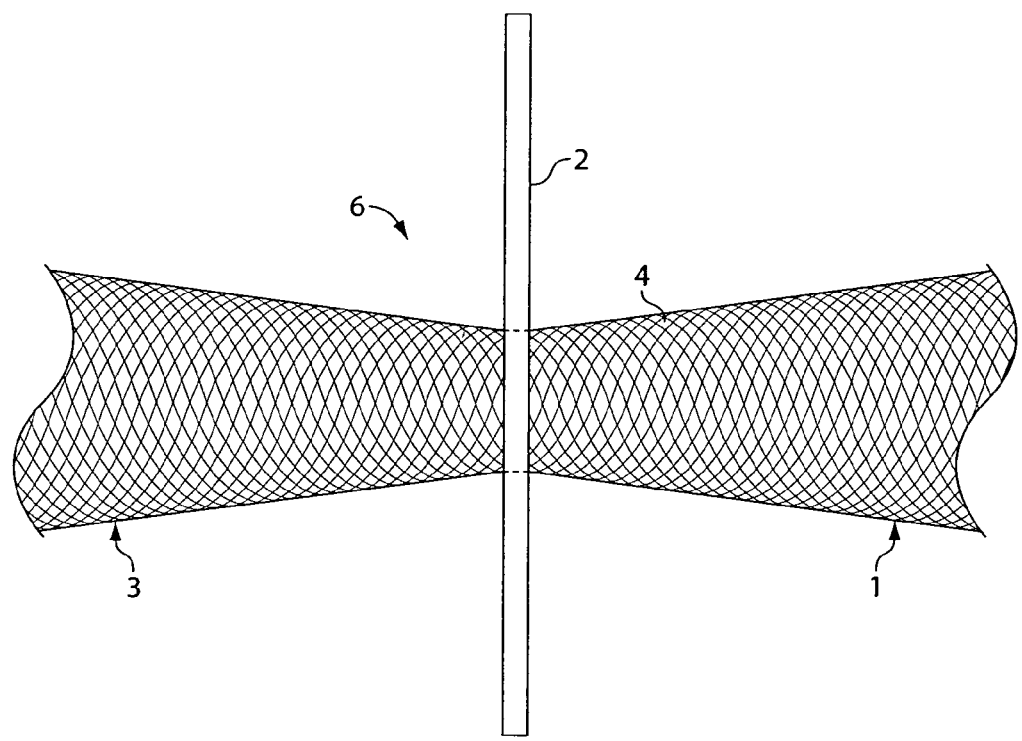
FIG. 4 is a diagram of a prototype high performance cannula according to one embodiment of the invention.
Figure 5:
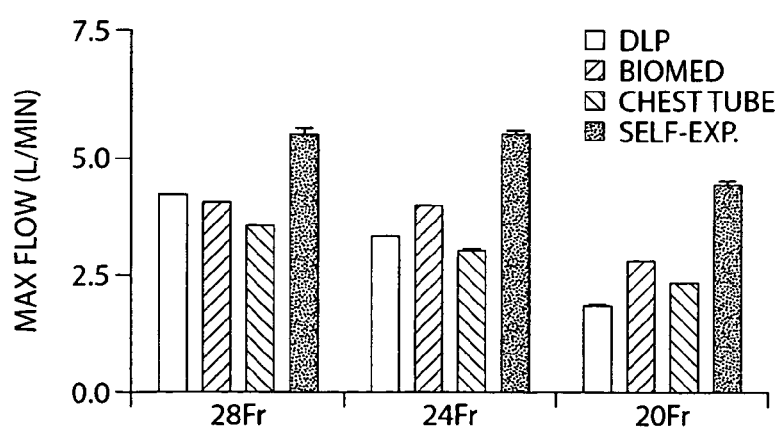
FIG. 5 is a histogram showing the results of in vivo comparison experiments measuring the flow rates through various commercially available cannulas and the high performance cannulas of the invention.

By "low profile conformation" is meant any conformation similar to that shown in FIG. 2B. According to one embodiment, illustrated in FIG. 2B, for example, the low profile conformation may be characterized by the cannula having a lumen diameter 5 at the point of insertion 2 that is greater than the lumen diameter 5 distal to the point of insertion 2. In its low profile conformation, a portion of the cannula 6 is characterized by a narrow diameter of the lumen 5 that is suitable for insertion into the object to be cannulated as well as into smaller access vessels. Placing the cannula in the low profile conformation of the cannula 6 can be achieved by the deformation of a shape memory metal, the deformation of an elastic, bendable, moldable, or flexible material; the activation of one or more diameter-varying mechanisms; and the deactivation of one or more diameter-varying mechanisms. One skilled in the relevant art will also recognize that placing the cannula in the low profile conformation can be done before, during, and/or after cannulation.

With any of the cannulas of the invention, in the normal profile conformation, the diameter of the lumen 5 at the point of insertion 2 can be narrower than the diameter at the proximal end 1 and/or the distal end 3. The diameter of the lumen 5 at the proximal end 1 and the distal end 3 may be the same or different. Typically, the diameter of the lumen 5 at the distal end 3 is greater than the diameter of the lumen 5 at the point of insertion 2. The diameter of the lumen 5 distal to the point of insertion 2 is either the same as the diameter proximal to the point of insertion 2 (i.e., the diameter of the lumen 5, in the normal profile conformation) or it expands to that of the surrounding vessel or environment.

By "proximal" is meant the external end of the cannula 6 that is not inserted into the object or vessel to be cannulated. Similarly, by "distal" is meant the end of the cannula 6 that is inserted into the object or vessel to be cannulated.

Turning now to the drawings, and to FIGS. 1-4 and 7-9 in particular, various embodiments of the cannula 6 according to the invention is shown. These cannulas 6 comprise a cannula body 4 having a proximal end 1, a distal end 3, and a lumen 5 having an internal diameter that extends between the proximal end 1 and the distal end 3.

In one embodiment, the cannula 6 is made of a flexible, deformable or moldable material that can be altered to allow the diameter of the lumen 5 to be varied. By "diameter of the lumen" is meant the diameter of the lumen 5 of the cannula body 4.

For example, the cannula body 4 may be made out of a plurality of flexible filaments that allows the diameter of the lumen 5 to be varied. The plurality of flexible filaments may be made of a material such as a plastic, a metal, a shape memory metal, an alloy, a synthetic fiber, a textile fiber, or any combination thereof. Those skilled in the art will recognize that a suitable material may be classified in more than one category. For example, a suitable material can be classified as both an alloy and a shape memory metal. Any of the flexible filaments may be wound into yam for use. Additionally, the materials may be interwoven or interlaced in any manner such as weaving, braiding or knitting.

The plurality of flexible filaments can contain more than one type of flexible filament. Further, the plurality of flexible filaments can be heterogeneously interwoven or interlaced. For example, the plurality of flexible filaments can be arranged to divide the cannula into segments along any axis such that the segments contain flexible filaments of different materials, or the segments contain the same flexible filaments arranged differently. For example, a cannula can be divided along its length into three or more segments (e.g., a "proximal segment", a "middle segment" and a "distal segment"). In this example, the proximal segment of the cannula body can include textile fiber flexible filaments while the distal segment includes stainless steel flexible filaments in order to provide stronger expansion force at the distal end. A cannula can include any number of segments, or can be unsegmented.

The plurality of flexible filaments can have any shape such as, for example, round, oval, flattened, triangular, rectangular, or any combination thereof. The shape and thickness of the flexible filaments can affect or influence the performance of the cannula. Additionally, the material of the flexible filament may also be spring-loaded or torsioned to further allow the diameter of the lumen 5 to be varied. Specifically, when the material is altered, e.g., stretched, spring-loaded, deformed, activated, compressed, and/or torsioned, the diameter of the lumen 5 is decreased. The diameter of the lumen 5 returns to its normal profile conformation (or to that of the surrounding vessel) upon termination of the alteration.

The plurality of flexible filaments of the cannula body can be made of one or more metals or alloys. Metals or alloys can provide a stronger expansion force (e.g., hoop strength) relative to other materials of the same size such as textile filaments. Because the diameter of metal or alloy flexible filaments can be smaller, while still achieving a certain desired expansion force, a cannula including a plurality of flexible filaments made from metals or alloys can have larger lumens relative to other cannulas having a similar external diameter. Thus, when constructing smaller diameter cannulas, e.g., 1-mm diameter cannulas, it may be preferable to use a plurality of metal flexible filaments such as surgical grade stainless steel. Those skilled in the art will recognize that shape memory metals, such as nitinol, are also able to provide stronger expansion force.

The plurality of flexible filaments can also be made of one or more synthetic fibers. Suitable synthetic fibers include, but are not limited to, rayon, acetate, polyester, nylon, acrylic, modacrylic, olefin, spandex and polypropylene, or combinations thereof.

Likewise, the plurality of flexible filaments can also be made of one or more shape memory metals. The term "shape memory metals" relates to metals and metal alloys that can undergo a solid state phase transformation from one crystal lattice structure to another crystal lattice structure. Because the metal molecules remain in a closely packed structure, the material remains in a solid state. The lower temperature phase is called the Martensite phase and is characterized by the shape memory metal being relatively soft and easily deformable. The higher temperature phase is called the Austenite phase and is characterized by the shape memory metal being relatively stronger. The phase transformation between the Martensite phase and the Austenite phase occurs over a temperature range denoted by the nomenclature:

$A_s$=Austenite start temperature
$A_f$=Austenite finish temperature
$M_s$=Martensite start temperature
$M_f$=Martensite finish temperature The temperature range of the phase transformation depends on characteristics such as the identity of the alloy and the relative composition. Altering these or other characteristics of the alloy can enhance operation of the cannula. For example, altering the processing of the shape memory metal can change the Austenite start temperature.

The molecular rearrangement of the crystal lattice structure results in two different properties: shape memory effect and superelasticity. The shape memory effect can occur when the shape memory metal is deformed in the Martensite phase. Upon heating above the Austenite finish temperature $A_f$, the shape memory metal undergoes a phase transformation into the Austenite phase, and assumes its original configuration.

Shape memory metals also possess a quality known as superelasticity or pseudoelasticity. Superelasticity occurs to shape memory metals substantially composed of its Austenite form. When a force is imposed on the shape memory metal, there is a phase transformation from the Austenite form to the Martensite form. When the load is decreased, the Martensite form transforms to the Austenite form.

Alloys with shape memory properties include, but are not limited to, nickel/titanium (also known as "nitinol"), copper/zinc/aluminum, copper/aluminum/nickel, silver/cadmium, gold/cadmium, copper/tin, copper/zinc, indium/titanium, nickel/aluminum, iron/platinum, manganese/copper, iron/manganese/silicon, and combinations thereof.

The shape memory and/or the superelastic properties of shape memory metals can be used in the plurality of flexible filaments of the cannula. For example, a cannula comprising flexible filaments made from one or more shape memory metals may be placed in it low profile conformation in the Martensite phase. Upon heating, either by body temperature or by an alternate heating source, the shape memory metal can exist in the Austenite phase and assume the normal profile conformation. In this embodiment, shape memory metals preferably have Austenite finish temperatures slightly less than body temperature. For example, the Austenite finish temperature can be between about 25° C. and 37° C., and preferably between 30° C. and 35° C. Similarly, in this embodiment, the Austenite start temperature is preferably between room temperature and body temperature.

Similarly, in an alternative embodiment, a shape memory metal in the Austenite phase can be placed in the low profile conformation by applying a stress to convert the metal to its Martensite phase. After the cannula is properly placed or inserted, the stress can be relieved and the material of the cannula undergoes a phase transformation to return the cannula to its normal profile conformation in the Austenite phase.

The plurality of flexible filaments of the cannula body can also comprise one or more textile fibers, which include natural or synthetic fibers that can be interlaced to create textiles. Cannulas using textile fibers within the plurality of flexible filaments may be preferable for high-volume and low-cost production of high performance cannulas. Common textile fiber-forming materials include, but are not limited to, cellulosics, e.g., linen, cotton, rayon and acetate; proteins, e.g., wool and silk; polyamides; polyester; olefins; vinyls; acrylics; polytetrafluoroethylene; polyphenylene sulfide; aramids, e.g., Kevlar or Nomex; and polyurethanes, e.g., Lycra, Pellethane and Biomer.

In order to manufacture some textile fibers, polymers can be extruded by techniques such as wet, dry, or melt spinning. The resulting extruded polymer is then processed to obtain the desired texture, shape, and size. By controlling morphology, textile fibers can be manufactured having different mechanical properties. Additionally, the component materials are unique in chemical structure and potential properties. The properties of the cannula can be altered by altering the shape of the textile fiber, the identity of the textile fiber material, the use of monofilaments or multifilaments, the amount of twist binding the textile fibers together, the orientation of molecules in the textile fibers, and the size of the textile fibers.

Flexible filaments used in the invention can be converted into yarns using any twisting or entangling processes that can enhance one or more characteristics. As used herein, the term "flexible filaments" also refers to flexible filament yarns. The plurality of flexible filaments can be interlaced by various processes such as weaving, knitting and braiding. Weaving the plurality of flexible filaments relates to interlacing the plurality of flexible filaments at an angle. For example, weaving the plurality of flexible filaments can include interlacing the plurality of filaments at 90° angles. Knitting the plurality of flexible filaments relates to intermeshing loops of the plurality of flexible filaments. Knitted flexible filaments include weft or warp knit flexible filaments. Braiding the plurality of flexible filaments relates to crossing sets of flexible filaments in a diagonal pattern. Braided products can also include tubular structures, with or without a core, as well as ribbon.

Additionally, the woven, braided or knitted pluralities of flexible filaments can be modified to enhance one or more properties. For example, weft-knitted structures are highly extensible when compared with woven fabrics, but they are also dimensionally unstable unless additional yarns are used to interlock the loops and reduce the extension while increasing elastic recovery.

The cannula 6 may also comprise one or more mechanisms that allow the diameter of the lumen 5 to be varied. Such mechanisms may be, for example, coils; springs; extensible, compressible, or releasable wings; foils; folds; and/or cages. However, one skilled in the art will recognize that other suitable mechanisms may also be employed. The cannula of the instant invention contains at least one mechanism that, upon actuation, serves to alter the cannula between a normal profile conformation and a low profile conformation. For example, when activated, the mechanism can place the cannula 6 in its low profile conformation, thereby decreasing the diameter of the lumen 5. Upon release of the mechanism, the cannula 6 will either return to its normal profile conformation or expand to the diameter of the surrounding vessel or environment. Alternatively, the activated mechanism(s) can maintain the cannula 6 in its normal profile conformation. Thus, in this embodiment, upon release of the mechanism, the cannula 6 is placed in its low profile conformation, thereby decreasing the diameter of the lumen 5.

Suitable mechanisms for altering the diameter of the cannula of the invention include, but are not limited to, a mandrel, an electric motor, a nano-engine, a change in pressurization, a wrapping string, a balloon, and a sheath. Those skilled in the art will recognize that these mechanisms may be used alone, or in combination with any other suitable mechanism(s).

When the mechanism is a mandrel, the cannula is placed in its low profile conformation by inserting the mandrel into the lumen of the cannula. After the cannula is appropriately placed or inserted within the object to be cannulated, the mandrel may be removed, thereby allowing the cannula to return to its normal profile conformation.

The mechanism may also be a sheath surrounding the cannula. Those skilled in the art will recognize that keeping the length of the cannula almost constant during expansion of the cannula is one advantage associated with compressing or collapsing the cannula from the outside.

Figure 6A:
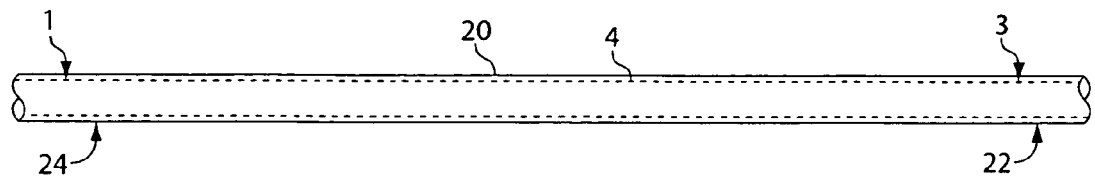
FIG. 6A illustrates a cannula according to one embodiment of the invention where the mechanism for altering the diameter of the cannula lumen is a sheath. In this figure, the sheath is positioned around the cannula body, thereby placing the cannula in the low profile conformation.

Referring to FIG. 6A, the cannula 6 is placed in the low profile conformation by placing the cannula body 4 within a sheath 20. The sheath may be any hollow structure that contains and maintains the cannula body 4 in the low profile conformation. For example, the sheath can compress the cannula into its low profile conformation and can provide a smooth outer surface for insertion and withdrawal of the cannula. The sheath can have any geometrical shape including circular, rectangular, oval, hexagonal, octagonal, and the like. The sheath may have a diameter less than the diameter of the cannula body 4 when in its normal profile conformation. Suitable materials for the construction of the sheath include, but are not limited to, polymers such as polyvinylchloride, polyurethane, polyethylene, polypropylene, polyamides; metals; metal alloys; and combinations thereof. The sheath may optionally contain holes and/or may be porous.

Figure 6B:
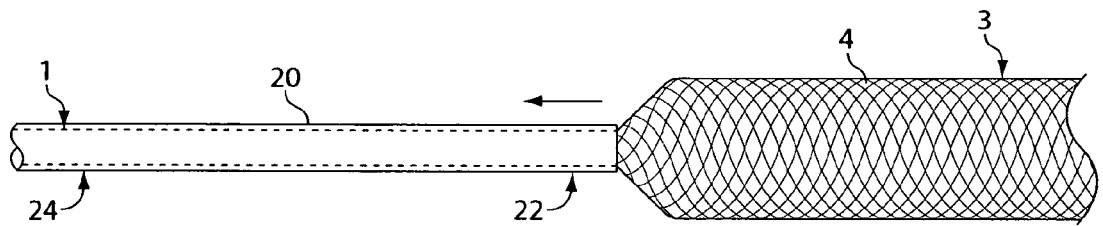
FIG. 6B illustrates a cannula according to the embodiment of FIG. 7A, where the sheath is partially withdrawn from the cannula.
Figure 6C:
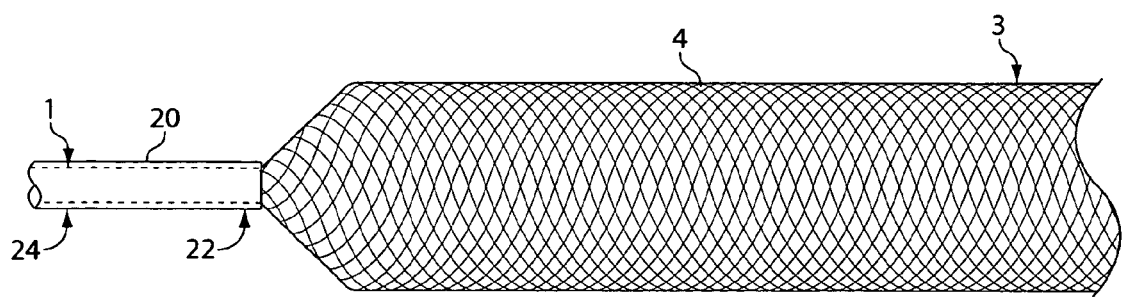
FIG. 6C illustrates a cannula according to the embodiment of FIG. 7A, where the sheath is fully withdrawn from the cannula, and the cannula is in the normal profile conformation.

As shown in FIG. 6A, the cannula 6 is placed into its low profile conformation by compressing, or otherwise containing, the cannula body 4 within the sheath 20. The cannula 6 may optionally have a means for securing the sheath 20 to the cannula body 4. The cannula 6 and sheath 20 are inserted at a point of insertion and the distal end 3 of the cannula body 4 is placed in the appropriate position within the object to be cannulated. Referring to FIG. 6B, the cannula 6 is returned to or placed in its normal profile conformation by withdrawing the sheath 20 proximally, as indicated by the arrow. As the sheath 20 is withdrawn, the distal end 3 of the cannula body 4 expands to the maximum diameter of the surrounding vessel or hollow organ, or to the maximum diameter of the cannula body 4 in the normal profile conformation. FIG. 6C shows the cannula 6 once returned to or placed in its normal profile conformation. Those skilled in the art will recognize that the sheath 20 may be removed by any suitable means known in the art. For example, the sheath 20 can be composed of a degradable or dissolvable material that breaks down after insertion of the cannula 6 in the object to be cannulated. Once the sheath 20 fully degrades or dissolves, the cannula 6 will be returned to its normal profile conformation.

Figure 7A:
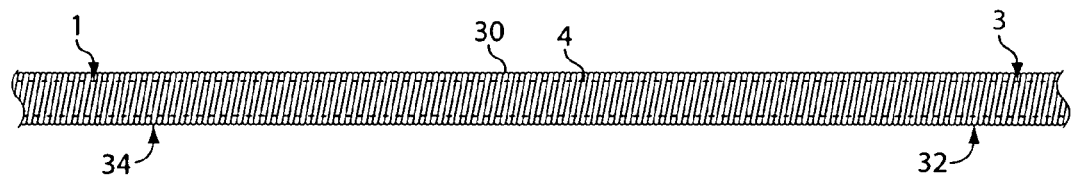
FIG. 7A illustrates a cannula according to one embodiment of the invention where the mechanism for altering the diameter of the cannula lumen is a wrapping string. In this figure, the wrapping string is positioned around the cannula body, thereby placing the cannula in the low profile conformation.

The mechanism may also be a wrapping string. Referring to FIG. 7A, the cannula 6 is placed in the low profile conformation by wrapping a wrapping string 30 around the cannula body 4. The cannula body 4 can be wrapped with a wrapping string 30 in any manner such as helically. Further, the wrapping string 30 can overlap, meet edge-to-edge, or have a gap between the loops of the string. In order to return the cannula to the normal profile conformation, the wrapping string 30 is unwound, unwrapped or otherwise removed from the cannula body 4.

Figure 7B:
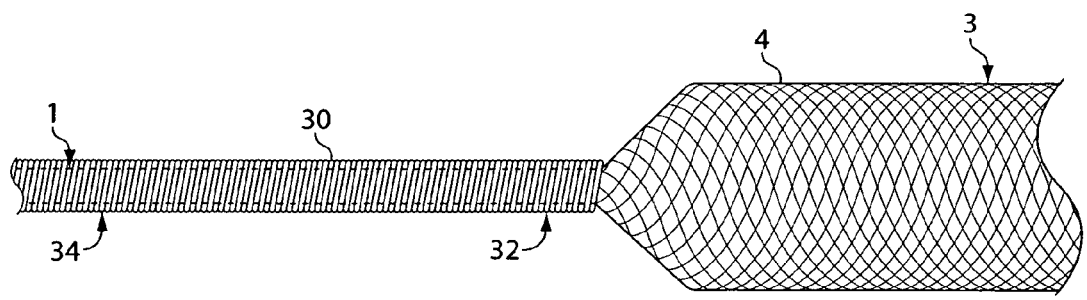
FIG. 7B illustrates a cannula according to the embodiment of FIG. 8A, where the wrapping string is partially withdrawn from the cannula.
Figure 7C:
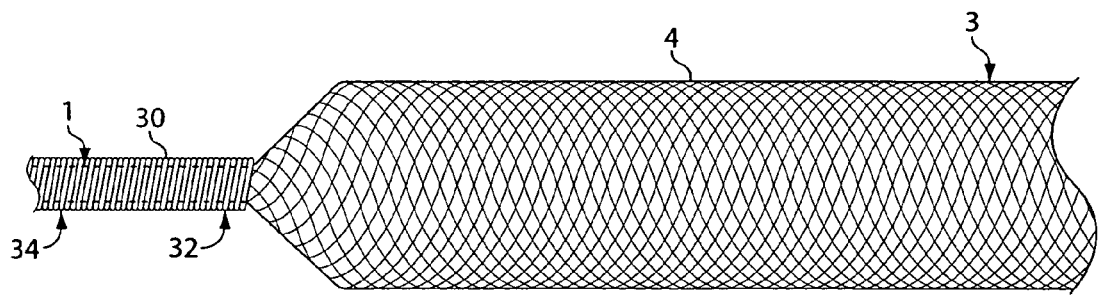
FIG. 7C illustrates a cannula according to the embodiment of FIG. 8A, where the wrapping string is fully withdrawn from the cannula, and the cannula is in the normal profile conformation.

The cannula body 4 can be unwrapped in several ways. Referring to FIG. 7B, the cannula body 4 can be unwrapped in a manner, such that the distal end 32 of the wrapping string 30 remains wrapped around the cannula body 4 and advances towards the proximal end. (e.g., the distal end of the wrapping string is slid proximally) As shown in FIG. 7C, only the distal portion 32 of the wrapping string 30 remains on the proximal portion 1 of the cannula body 4.

Alternatively, the cannula body 4 can be wrapped in a manner such that the distal end 32 of the wrapping string 30 remains wrapped around the cannula body 4 and remains at the distal end 3 of the cannula body 4. As the cannula body 4 is unwrapped, the wrapping string 30 is removed from the proximal end 1 of the cannula body 4. When the cannula body 4 is substantially unwrapped, only the distal portion 32 of the wrapping string 30 remains on the proximal portion 1 of the cannula body 4 following removal.

In yet another embodiment, the wrapping string is configured in such a manner as to unwrap from the distal portion 3 towards the proximal portion 1 of the cannula body 4. As the cannula body 4 is unwrapped, the wrapping string 30 is removed from the distal end 3 of the cannula body 4. When the cannula body 4 is substantially unwrapped, only the proximal portion 32 of the wrapping string 30 remains on the proximal portion 1 of the cannula body 4.

Those skilled in the art will recognize that other suitable means of removing the wrapping string may also be used. The wrapping string may comprise one or more materials such as metal, plastic, synthetic fibers and biodegradable fibers. For example, the wrapping string can comprise a quickly degrading material such that the wrapping string degrades or dissolves after insertion. Additionally, the wrapping string can have any width or thickness consistent with the scale of the object to be cannulated.

Figure 8A:
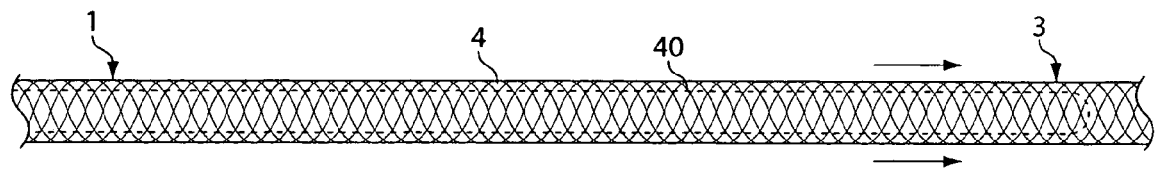
FIG. 8A illustrates a cannula according to one embodiment of the invention where the mechanism for altering the diameter of the cannula lumen is a balloon. In this figure, the cannula is in its low profile conformation.
Figure 8B:
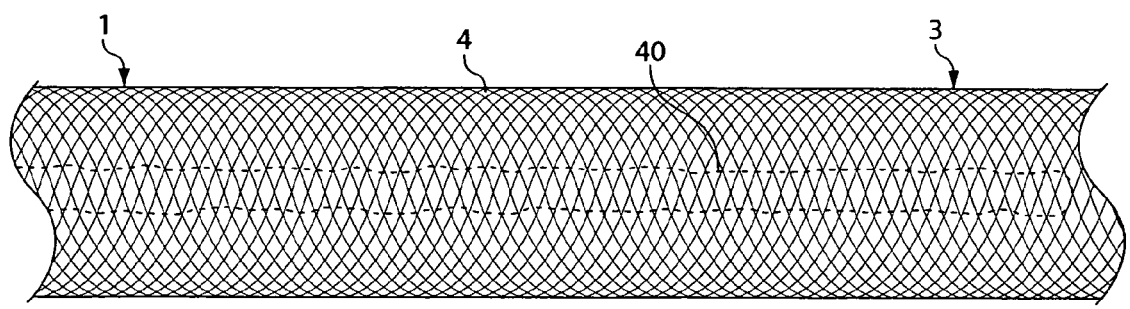
FIG. 8B illustrates a cannula according to the embodiment of FIG. 9A, where the balloon returned the cannula to its normal profile conformation.

The mechanism may also be a balloon. Referring to FIG. 8A, the cannula body 4 is placed in the low profile conformation by inflating a balloon 40, which exerts a force in the distal direction. As the balloon 40 exerts the force, the cannula body changes from the normal profile conformation to the low profile conformation. Referring to FIG. 8B, after the cannula is positioned, the balloon 40 is collapsed and the cannula body 4 returns to the normal profile conformation.

Alternatively, the balloon 40 can be used to return the cannula to its normal profile conformation from the low profile conformation. The cannula body 4 may be placed in the low profile conformation by the actuation of a suitable mechanism. The cannula body 4 is inserted at a point of insertion. When the cannula body 4 is in the appropriate location, the balloon can be inflated in order to return the cannula body to its normal profile conformation. After the cannula body is returned to the normal profile conformation, the balloon may optionally be deflated and removed from the cannula body. Alternatively, the deflated balloon may remain within the lumen.

Those skilled in the art will recognize that the balloon can be any shape as long as the shape allows the balloon to exert a force in the direction necessary to alter the conformation of the cannula. The balloon can be inserted into the object to be cannulated simultaneously with the cannula, or the balloon can be inserted into the lumen of the cannula after the cannula is positioned, or inserted, in the object to be cannulated.

The conformation of the cannula can also be altered by changes in pressurization. For example, the cannula body 4 is placed in the low profile conformation by applying pressure in the distal direction. As the pressure exerts force in the distal direction, the cannula body changes from the normal profile conformation to the low profile conformation. After the cannula is placed or inserted, the pressure is discontinued or altered such that the cannula returns to the normal profile conformation.

Alternatively, pressurization can be used to return the cannula to its normal profile conformation from the low profile conformation. The cannula body 4 may be placed in the low profile conformation by the actuation of a suitable mechanism. The cannula body 4 is inserted at a point of insertion. When the cannula body 4 is inserted in the appropriate location, pressure can be exerted in order to return the cannula body to its normal profile conformation. After the cannula body is returned to the normal profile conformation, the pressure may be discontinued.

The mechanism may also include an electric motor or a nano-engine. The electric motor or nano-engine can be coupled to any suitable mechanism such as, for example, coils; springs; extensible, compressible, or releasable wings; foils; folds; cages; mandrels; balloons; and a sheath. The electric motor or nano-engine can drive the mechanism, which alters the cannula between its low profile conformation and its normal profile conformation. Similarly, the electric motor or nano-engine can be coupled to a device that exerts a force on the cannula to alter the cannula between its low profile conformation and its normal profile conformation. For example, the electric motor or nano-engine can be coupled to a fan that provides pressure that alters the conformation of the cannula.

High-performance cannulas according to the invention can have plastic properties and/or elastic properties. Additionally, the cannula can be segmented into portions having plastic properties and other portions having elastic properties. As used herein, the term "elastic" relates to materials that deform in a recoverable way until a failure point is reached. Conversely, as used herein, the term "plastic" relates to materials that deform in a non-recoverable manner. A cannula can comprise elastic materials, plastic materials or combinations thereof. Those skilled in the art will recognize that a cannula manufactured from a elastic material(s) can be deformed and will return to its original conformation upon release. Alternatively, a cannula manufactured from a plastic material(s) will not return to its original conformation after deformation. The choice of elastic or plastic material(s) depends on the specific desired function of a particular cannula. For example, a portion of a cannula can be made of a plastic material in order to support the surrounding vasculature, while the remaining portions may be more elastic in nature.

Figure 1C:
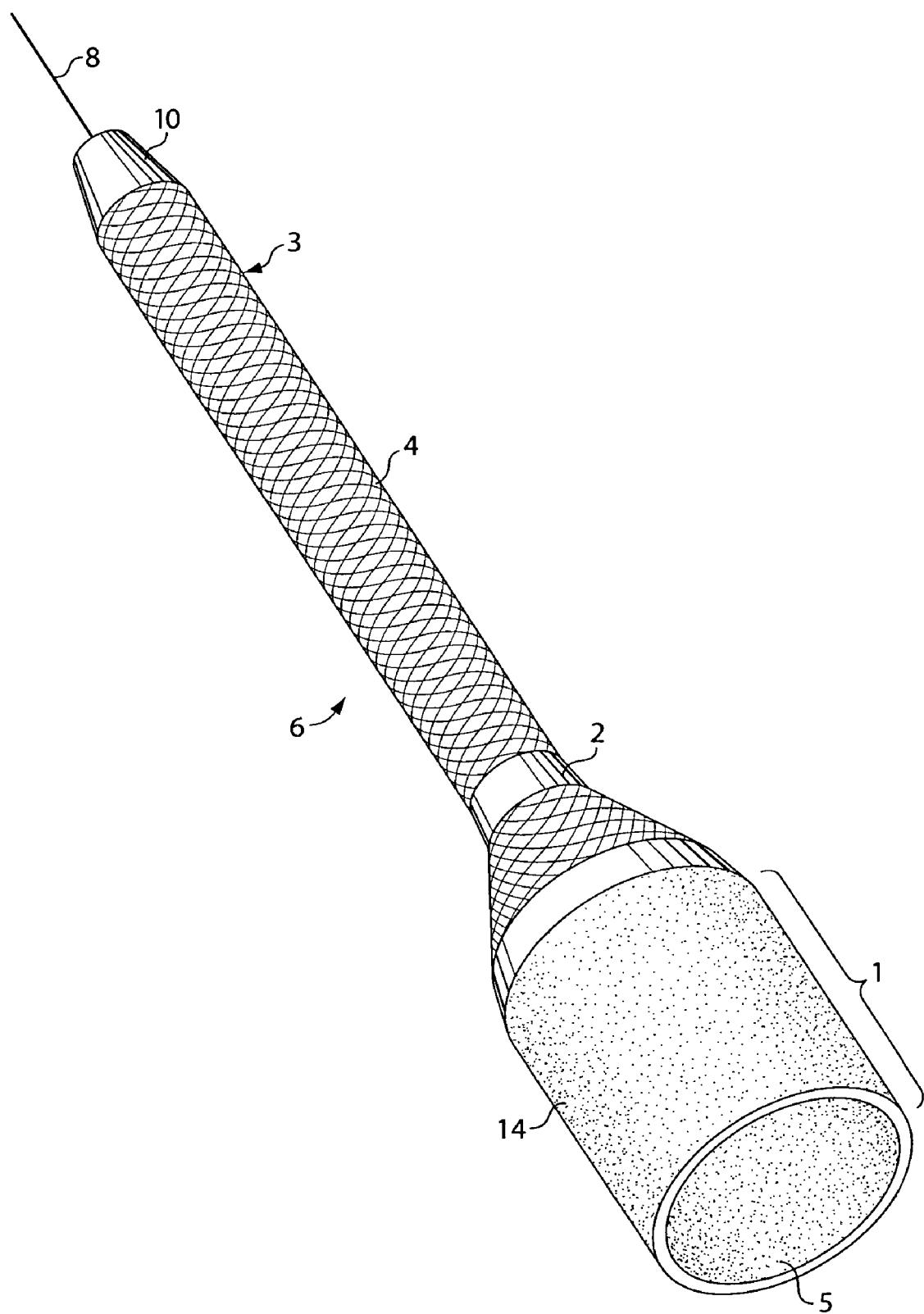
FIG. 1C illustrates a cannula according to one embodiment of the invention.

Additionally, at least a portion of the material comprising the cannula body 4 may be coated with a watertight coating. As illustrated in FIG. 1C, a layer 14 of watertight coating is depicted on the surface of cannula 6. For example, the watertight coating can be a plastic (such as plastic). However, those skilled in the relevant arts will recognize that any suitable watertight coating may also be used. In one embodiment, the layer 14 of watertight coating covers the entire cannula body 4. Alternatively, in a separate embodiment, the layer 14 of watertight coating only covers the proximal end 1 of the cannula body 4, or only covers certain segments of the cannula body. For example, the cannula can be designed such that it contains alternating areas of coated and uncoated segments.

Also provided are cannulas having a dual lumen, which can be used to carry two materials. For example, in hemodialysis, a dual lumen cannula can be used such that the lumen of the first cannula body (i.e., "first lumen") can be used for suction (e.g., towards an artificial kidney) and the lumen of the second cannula body (i.e., "second lumen") can be used for reinjection (e.g., return of processed blood towards the patient) or vice versa.

Figure 9:
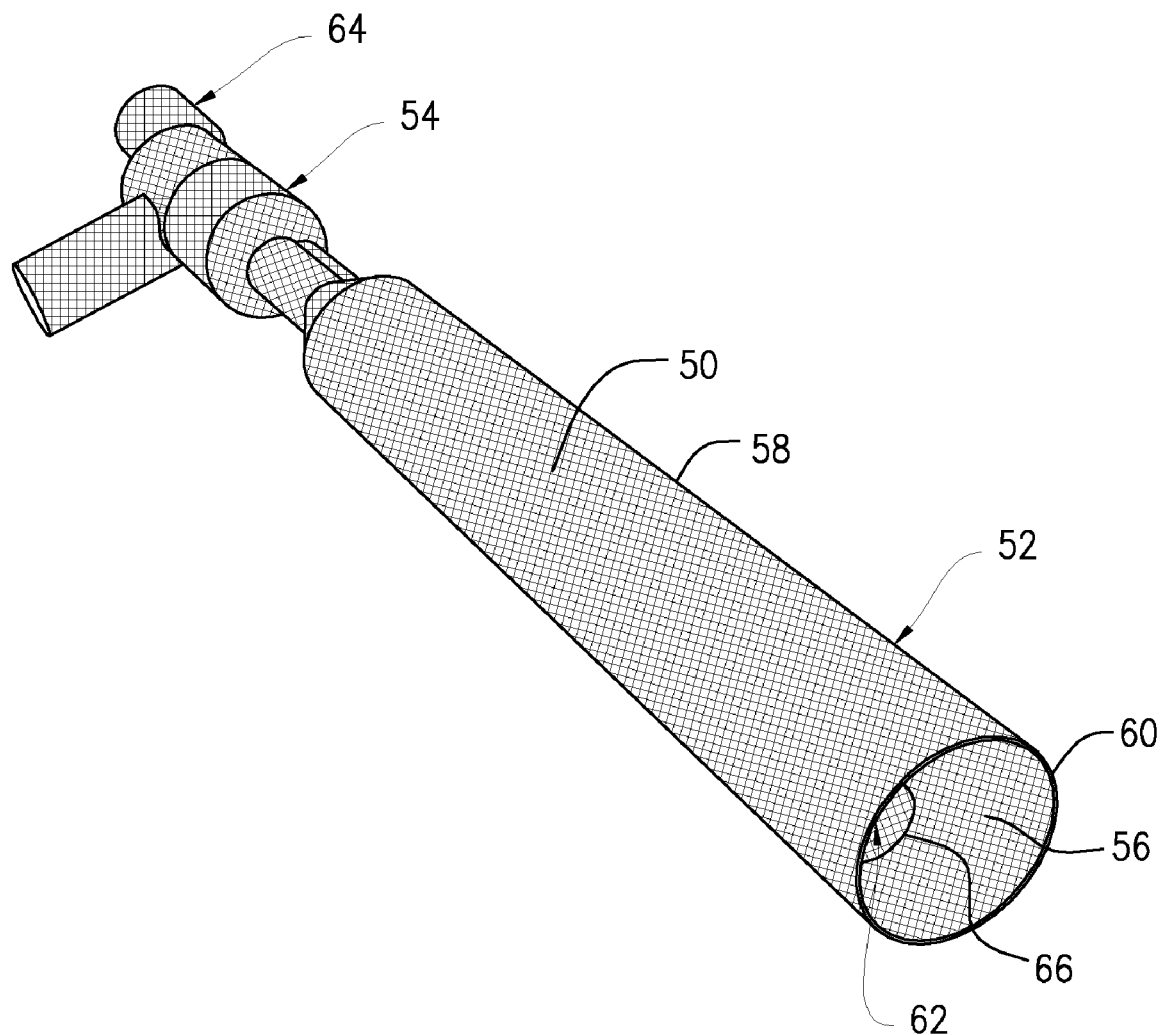
FIG. 9 illustrates a dual lumen cannula according to one embodiment of the present invention.
Figure 10:
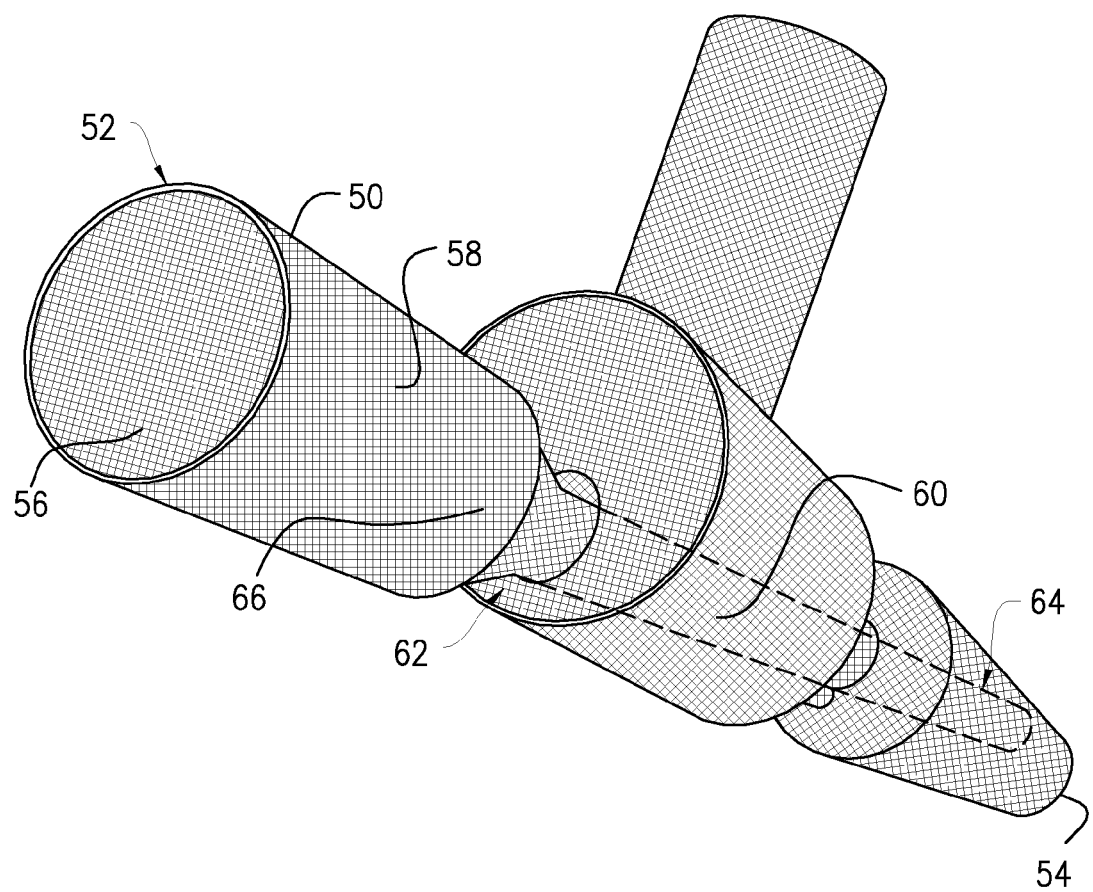
FIG. 10 provides a transparent view of the dual lumen cannula shown in FIG. 10.
Figure 11:
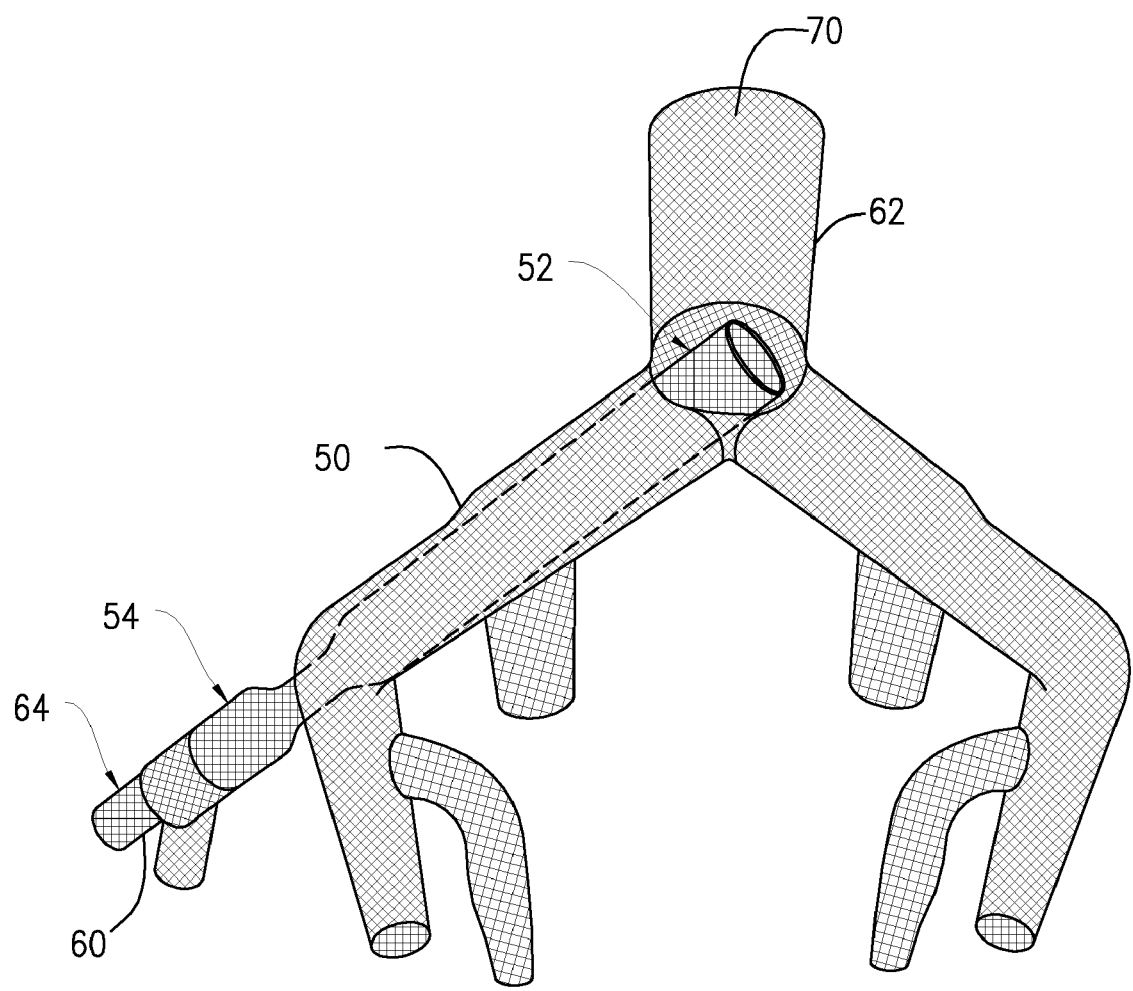
FIG. 11 illustrates the cannula of FIG. 10 in its normal profile conformation after insertion into the vasculature.

The first and second cannula bodies can be positioned coaxially or adjacently. Referring to FIGS. 9 and 10, when the first and second cannula bodies are positioned coaxially, a first cannula body 50, which includes a distal end 52 and a proximal end 54, surrounds a second cannula body 60, which also includes a distal end 62 and a proximal end 64. The distal end 62 of the second cannula body 60 can extend beyond the distal end 52 of the first cannula body 50, or can remain within the first cannula body 50. The second cannula body 60 can be positioned anywhere within the lumen 56 of the first cannula body 50, i.e., the second cannula body 60 can be centered or offset within the lumen 56 of the first cannula body 50. The terms "first cannula" and "second cannula" do not connote orientation. For example, the first cannula body can be the surrounding cannula body or the surrounded cannula body. The first cannula and the second cannula may both be a cannula of the present invention or one may be a traditional cannula. Preferably, when configured coaxially, the outer cannula is the cannula according to the present invention.

Alternatively, the dual lumens 56 and 66 can be located adjacently rather than coaxially. When located adjacently, the first cannula body 50 and the second cannula body 60 can be the same or different diameters when in the normal profile conformation. Similarly, the lengths of the first cannula body 50 and the second cannula body 60 can be the same or different, and the cannula bodies can be made of the same or different materials.

When located adjacently, a portion of the first cannula body 50 can be coupled to a portion of the second cannula body 60 by any means known in the art including, but not limited to, stitching, adhesive, solder, and/or mechanical coupling. Further, the first cannula body 50 can share at least a portion of its body with the second cannula body 60. This sharing can occur throughout the length of the cannula bodies, intermittently along a length of the cannula bodies, or a single spot on the cannula bodies. Additionally, the first cannula body 50 and second cannula body 60 can be arranged such that they are formed by a septum dividing two sides of a larger cannula body. In such an arrangement, the first cannula body is formed from a portion of the larger cannula body and one side of the septum while the second cannula body is formed from another portion of the larger cannula body and the other side of the septum. Alternatively, there may be two septums within the larger cannula body such that the first cannula body is formed from the larger cannula body and one septum, and the second cannula is formed from the larger cannula body and the other septum.

Further, the first septum can share a portion of its surface with the second septum. This sharing can occur throughout the length or width of the septums, intermittently along the length of the septums, or at a single portion of a surface of each of the septums.

There are various methods of using the dual lumen cannulas described herein. For example, a first cannula according to the invention can be placed in its low profile conformation, inserted into the patient or object to be cannulated and returned to its normal profile conformation. A second cannula according to the invention can then be placed inside the first cannula to create two coaxial lumens. Alternatively, the second cannula is collapsed within the first cannula prior to cannulation. Both the first cannula and second cannula can be returned to their normal profile conformation after insertion into the patient or the object to be cannulized. Those skilled in the art will recognize that the same or different mechanisms can be used to alter the conformation of the interior and exterior lumen.

Alternatively, a first cannula can be inserted into a patient and the lumen of the mandrel can be used as second lumen. The outer cannula can be placed in its low-profile conformation and inserted into the patient or the object to be cannulized. Once properly positioned, the cannula is returned to its normal profile conformation. The mandrel used to alter the conformation of the cannula also contains a lumen. After returning the outer cannula to the normal profile conformation, the mandrel is kept within the lumen of the cannula to create a coaxial dual lumen.

Figure 12A:
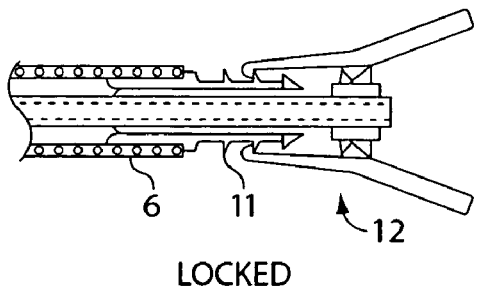
FIG. 12A illustrates a locking mechanism suitable for use with the high performance cannulas of the invention.

Any of the high performance cannulas described herein can also include a connector on its proximal end. In FIG. 12A, a cannula 6 is illustrated with connector 11. The connector 11 may be secured with a locking mechanism 12 or a plug. One skilled in the art will recognize that the plug can comprise any shape or material suitable for securing the connector. Alternatively, the connector 11 may be replaced by a flexible (silastic: e.g., 10 cm.) tube, which allows for clamping of the cannula (at the level of the flexible tube) without damage. Additionally, a user could select a connector in accordance with the diameter of the line tubing utilized (cannula-connector line). The proximal end of the cannula may additionally (or alternatively) contain a connecting sleeve rather than a connector. The connecting sleeve can couple the cannula to a perfusion system or other device. The connecting sleeve can comprise any shape, size or material suitable for coupling the cannula to an external device. Additionally, the connecting sleeve may be configured to couple a cannula with a device, wherein the cannula and device have a different diameter, cross-sectional width, and/or size.

According to another embodiment of the invention, a mandrel may be mounted on a porous plug. The porous plug permits the passage of air necessary for venting the cannula. In one implementation, the mandrel is hollow and may be mounted in the porous plug. The porous plug may further be perforated so as to allow a guidewire (passing through the cannula tip and into the mandrel) to exit therethrough. The porous plug, together with the mandrel, preferably fits snugly into the flexible tube (used in place of the connector, as described above) at the cannula end. Hence, the cannula may be collapsed with the plug-carrying mandrel, and may further remain in this configuration due to the snug fit of the porous plug in the flexible tube.

The cannulas of the invention can also include one or more additional devices to increase the functionality and/or performance of the cannula. For example, the cannula can include one or more microturbines, which can provide enhanced capabilities such as increasing the flow rate of fluids through the cannula. The cannulas of the invention may also include one or more sensors, which can be coupled to various portions of the cannula to enhance performance or functionality. Sensors coupled to one or more microturbines can be used to adjust and/or maintain the output of the turbine. Similarly, sensors can be coupled to any suitable mechanism that can be used to change or alter the diameter of the lumen. For example, the cannula can include sensors coupled to small electric motors to facilitate telemanipulation of the cannula.

The cannulas according to the invention are characterized by a high rate of fluid flow through the lumen 5. Specifically, the rate of fluid flow through the lumen 5 is between 1 mL/min and 100 L/min. Preferably, the rate of fluid flow is between about 100 mL/min and about 6 L/min. When used in connection with cardiac surgery, typical fluid flow rates through the cannula 6 are between about 100 mL/min and 6 L/min. When used during dialysis, or hemofiltration, typical fluid flow rates through the cannula 6 are between about 100 mL/min and about 500 mL/min. When used for intravenous delivery of fluids, typical fluid flow rates through the cannula are between about 1 mL/min and about 10 mL/min. Thus those skilled in the art will recognize that the use of the cannulas according to the invention is desirable for any application where a continuous fluid flow is required.

The cannulas according to the invention can be a variety of sizes. For example, they can be miniaturized for use in the cannulation of small vessels or objects. Alternatively, they can be enlarged for cannulation of larger vessels or objects. Those skilled in the art will be able to routinely select an appropriate sized cannula.

Method of Using High Performance Cannulas

The invention also provides methods for using the high performance cannulas according to the invention. For example, the cannula 6 can be placed in its low profile conformation, inserted into the object to be cannulated, and returned to its normal profile conformation. In some embodiments, in the normal profile conformation, the cannula 6 returns to its original shape and diameter distal to the point of insertion 2. In other embodiments in the normal profile conformation, the cannula 6 expands up to the internal diameter of the surrounding vessel or environment distal to the point of insertion 2. When used according to these methods, the cannulas of the invention result in a smaller access aperture than other traditional cannulas that are commonly used for cannulation. Advantageously, this smaller access aperture does not adversely impact the flow rate of fluids through the cannula 6.

When used according to the methods of the invention, the conformation of the cannulas 6 of the invention can be altered before, during, and/or after cannulation.

Cannulas according to the instant invention can be used in a variety of medical and non-medical contexts. For example, the methods outlined above can be used for percutaneous insertion, central cannulation, tracheal tubes, chest tubes, drainage catheters, heart surgery, and dialysis as well as in any non-medical or extramedical situations or applications in which a continuous fluid flow and a small access aperture are desirable. Those of ordinary skill will recognize that the cannulas according to the invention will be suitable for a variety of purposes where a minimally invasive means of obtaining a continuous flow of fluids is desired.

Because of the ability to decrease the diameter of the lumen 5 of the cannula 6 at the point of insertion 2 without impacting the flow rate of fluids through the cannulas, the cannulas according to the invention are particularly suitable for use in minimally invasive procedures (in both medical and non-medical contexts) and/or surgeries. By way of non-limiting example, the cannulas of the invention can be used for blood gas measurement and for establishing a continuous shunt.

The cannulas according to the invention may be included as a part of a high performance cannulation kit. For example, the kit may include a sharp hollow needle, a J-type guidewire 8, a set of dilators, a mandrel 7 having a locking mechanism 12, and the high performance cannulas of the instant invention packaged together. Those skilled in the relevant arts will recognize that kits comprising additional elements can also be used.

Medical Uses

The high-performance cannulas of the invention can be used in a variety of medical uses and contexts. Those skilled in the art will recognize that the high performance cannulas described herein can be used for insertion into any hollow organ such, as a vein, an artery, a urethra, a ureter, an intestine, an esophagus, a trachea, a bronchial tube, a pleural space, and a peritoneum. As used herein, the term "hollow organ" refers to any structure containing a lumen, and can include vessels within solid organs such as kidneys. Further, the cannula can be inserted through an orifice and/or through an incision in the skin.

Arterial Cannulas

One advantage provided by a self-expanding venous cannula (which may be collapsed to a lower profile prior to insertion), is an increase in the volume of blood flow through the cannula coupled with a decreased pressure drop, and a decrease in shear stress. These characteristics are also of interest for efficient blood return via an arterial cannula, which can change its shape once positioned in situ. For a given access aperture on the arterial side, an application of the high flow cannula design described herein (i.e., collapsed insertion and self-expansion in situ) has, in addition to a decreased pressure drop, the additional advantage of diminishing the velocity of the blood jet at the cannula outlet. This reduces the danger of high-velocity jet-lesions of the aortic wall, as well as the potential for aortic wall plaque mobilization and secondary embolization.

Access to the Veins and Arteries

Access catheters are generally necessary for transfusion of fluids, plasma-expanders, blood components or substitutes, and/or for taking measurements. Typical applications include massive volume infusions for patients in circulatory collapse (shock). Under such circumstances, the peripheral target vessels are usually collapsed (e.g., empty due to a lack of circulating blood) and constricted (e.g., due to low cardiac output, centralization, and/or high levels of circulating vaso-constricting agents). Thus, puncturing such collapsed and/or constricted small access vessels may be difficult. Hence, small-bore catheters are usually preferred.

However, one drawback associated with the use of small-bore catheters is that their small luminal diameter may serve to limit flow through the catheter. As such, large-volume transfusions over a short time period may be difficult and/or prolonged, and this may be detrimental for a patient.

To remedy this and/or other drawbacks associated with the use of small-bore catheters, high flow access catheters based on the high flow cannula design described herein (e.g., collapsed insertion and self-expansion in situ) may be used. Specifically, the high flow access catheter may comprise a flexible, elastic plastic catheter that can be stretched over a hollow mandrel in order to be made thinner for introduction over a guide-wire. Upon removal of the mandrel, the catheter will expand to its initial diameter, which may be larger than the diameter at the point of insertion. In some embodiments, the lumen of the catheter may be enlarged (e.g., expanded) over its entire length (either fully or in part).

The high flow access catheter may be stretched over a centrally-positioned mandrel in a number of ways. For instance, the diameter of the tip orifice of the catheter may be smaller than the diameter of the mandrel. Alternatively, other mechanisms (e.g., bars, cams, hooks, etc.) may be used to keep the mandrel within the desired position of the tip of the catheter during loading and insertion. Examples of such mechanisms may include, but are not limited to: (1) a conically shaped tip with central and lateral holes; (2) a two-or-more stage design with or without lateral holes; (3) a tapered design with lateral slits that open when the catheter is expanded or pressurized; and (4) a flexible grid design similar to the one described for the high flow cannulas.

Any suitable mechanisms that allow for increased cross-sectional area of the catheter following insertion may be employed. Such mechanisms may include, but are not limited to, foils, springs, coils, folds or other suitable mechanisms, and those skilled in the art will routinely be able to select a suitable mechanism. Any designs and/or mechanisms, which aid in establishing a shorter, narrow path once the catheter (or cannula) is in its expanded, inserted position may result in higher fluid transfer rates through the catheter (or cannula).

Hemofiltration/Dialysis

The cannulas and access catheters described herein may also be modified for use in hemofiltration and dialysis. During hemofiltration and dialysis, efficient blood purification is mainly limited by the volume of blood flow that can be achieved. In contrast to the access situation for rapid transfusion, where one main goal is to enable transfer of a high volume of blood to the patient within a short time frame, hemofiltration and dialysis typically require two lines: (1) one for blood withdrawal; and (2) one for blood return. Small bore catheters tend to limit flow more on the blood-collecting side where negative pressure is usually required to increase flow (e.g., risk of donor vessel and/or line collapse) as opposed to the arterial side, wherein the positive pressure used helps to keep the line and the recipient vessel open.

Two high performance cannula-type catheters designed for collapsed insertion and expansion in situ can be used. For example, the dual lumen cannulas described herein may be used. In certain embodiments, a coaxial design having only one vessel puncture for blood drainage and return may be used. However, those skilled in the art will also recognize that the two catheters may be positioned adjacently. Various design options also exist for coaxial dual-lumen catheters which may be collapsed for insertion, including, for example, a dual-lumen catheter comprised of two collapsible catheters, one within the other. In one embodiment, the inner lumen (which may be used for returning the blood and may therefore have a positive pressure load) may be made of soft, collapsible flexible material. Such a material may have little or no ability to self-expand. Blood may serve to unfold the inner lumen as it is pumped through the inner lumen. Blood may drain through the outer lumen and return through the inner lumen, or vice versa, according to various embodiments.

Alternatively, two separate catheters may be provided. A first, basic self-expandable venous catheter may be used for collecting blood, and a second, return catheter may be inserted in a coaxial position, rather than using a mandrel for stretching the cannula. The latter design may employ a special manifold that enables the separation of the two blood flows (peripheral versus central), to connect them to the tubing flowing toward and away from the pump, respectively.

Trachea (Transoral, Transnasal)

The high flow cannula principles and embodiments described herein may also be applied to tracheal intubations. Advantages associated with this use include, but are not limited to: (1) providing one self-expanding tube that can fit several sizes; (2) enabling a self-expanding cannula to expand to the optimal diameter for a given trachea; (3) enabling superior intraluminal air flow by freeing up the space that is typically occupied by balloons in associated with known procedures; (4) enabling the portion of the self-expanding tube sitting within the trachea to be uncovered, thus allowing for spontaneous ciliary motion and mucus transportation in this area; and (5) enabling the self-expanding tracheal tube to be inserted over a guide wire.

Stretching the tube over a hollow mandrel may be required to collapse the self-expanding tube prior to insertion into a trachea.

In contrast to the self-expanding cannula wherein the presence of a conical tip may not impede blood flows, both ends of a tracheal tube should remain open as widely as possible to allow for an optimal bronchial opening. To achieve this, the wires (or plurality of flexible filaments) of the grid structure of the tracheal cannula (or expanding tracheal tube) may form a loop at the tracheal end of the tube. These wires can be captured by hooks or filaments, etc., and can be kept close to the tip of the mandrel (covered by a cap if necessary) during insertion of the tracheal tube.

Tracheotomy

The technology outlined above for a high flow inter-tracheal tube may also be applied for tracheotomy tubes. The dimensions of the high-flow inter-tracheal tube may be adapted for such an application, and the tip for the collapsed condition may be modified for percutaneous insertion over a guide-wire following dilation with serial dilators.

Non-Medical Uses

Those skilled in the art will recognize that the cannulas of the invention can be used in many non-medical applications involving transporting materials such as fluids, powders and gases through pipes or tubes, which often have a fixed diameter resulting from a specific access aperture configuration. In such a situations, a traditional approach to filling or emptying a tank (or other vessel) is selecting a pipe or tube having a diameter equal to or less than the diameter of the access orifice. Although tubing with a relatively small cross sectional area compared with its length results in a significant pressure drop, the use of more powerful pumps usually addresses the resulting flow limitation. This approach tends to be effective when using positive pressure, because the maximum pressure is primarily limited by the strength of the tubing wall and of the media to be transported.

However, when using negative pressure, other considerations must be taken into account. First, some fluids are not resistant to negative pressures (e.g., vaporization, loss of biological activity, etc). Second, the maximum negative pressure is limited. Consequently, pressure drops resulting from a small cross sectional area, which in turn is a function of a small access orifice, is more of an issue.

The use of the cannulas of the invention (e.g., cannulas with collapsed insertion and in situ expansion) provides significant advantages in many technical applications where a short narrowing of a path for fluids or other media allows for significantly higher flows in comparison to longer narrow paths.

The cannulas of the invention can be used to fill and empty (through a narrow orifice) mobile tanks such as those found in, for example, cars, trucks, ships, planes, tanker-planes and other vehicles. For example, a cannula of the appropriate size can be placed in the low profile conformation and inserted into the tank. The cannula can then be returned to its normal profile conformation and the tank can be filled or emptied.

The cannula can also be used to fill or empty fluids, or media exhibiting fluid-like behavior, from fixed tanks such caverns or silos. Examples of fluids, or media exhibiting fluid-like behavior include, but are not limited to water, gasoline, kerosene, fuel, crude, vapor, gases, powder, grains, rice, beans, and the like.

The characteristics of the specific cannula used in non-medical contexts can vary depending on the object to be cannulated. Those skilled in the art will recognize that, for industrial applications, the diameter of the cannula in its normal profile conformation can be very wide. Similarly, the cannulas can be made of stronger and more durable, flexible materials.

Emptying a tank from the top through a narrow access aperture requires a tube passing through the narrow access to the bottom of the tank. Consequently, the expanding portion of the cannula within the tank should be tightly covered over a substantial portion of the length within the tank. However, it is not necessary for the cover to couple or attach directly to the tube body, which can be any type of expandable scaffold or grid that provides a lumen. In negative pressure applications, the cover can be loosely coupled to the expandable scaffold such that the resulting suction draws the cover onto the scaffold and draws the liquid through the tube from the open end. In positive pressure applications, once the cover is appropriately positioned, the scaffold can optionally be removed, as the pressurized fluid will maintain the cover.

Methods of Making High Performance Cannulas

Cannulas can be manufactured by a variety of methods. For example, the plurality of flexible filaments of the cannula body can be interlaced or interwoven by weaving, braiding or knitting. One skilled in the art will recognize the various automated and non-automated methods for interlacing or interweaving can be employed. The resulting interlaced plurality of flexible filaments can form, for example, a grid- or mesh-like structure that can have its diameter varied.

Alternatively, a similar grid- or mesh-like configuration of a plurality of flexible filaments may be made by etching, cutting or otherwise removing portions of a continuous open-ended body, e.g., a tubular body. For example, the continuous body may comprise materials such as plastic, metal and shape memory metal. Portions of a continuous tube can be removed, by laser-cutting or water-cutting the tube, to create the appropriate grid-like structure. The resulting plastic cannula is expandable to a larger diameter (compared to the diameter in its low profile conformation) in situ.

Alternatively, the cannula can be manufactured by injection molding. The materials comprising the plurality of flexible filaments are liquefied by heating, chemical means or other means, and injected into a suitable molding. Similarly, the cannula body can be manufactured by extrusion. Any of the above manufacturing processes can be combined to create a suitable cannula.

To accelerate the manufacturing process, a photo-activated material may be used for potting the wires or filaments of the grid at a tip of the cannula. For example, the flexible filaments may be potted at the distal end of the cannula with a photo-activated epoxy, which works faster than other potting materials.

The invention will be further described in the following examples, which do not limit the scope of the invention described in the claims.

Example 1

In Vivo Cannula Comparisons

In vivo experiments in bovine were conducted to compare the flow rate of fluids through the high performance cannula 6 of the invention and other commercially available cannulas of various diameters. Specifically, the comparisons involved the cannulation of the superior vena cava (the target vessel) through the jugular vein (the access vessel) after calibration of the aperture (through which the cannula and blood flow have to pass) access to 28 French (9.33 mm), 24 French (8 mm), and 20 French (6.66 mm) cannulas. The cannulas tested included DLP cannulas (Medtronic), Biomedicus cannulas (Medtronic), generic chest tube cannulas, and the high performance cannulas according to the instant invention. To insure standardized conditioning, gravity drainage was set at 60 cm of water for each of the cannulas tested.

The results of the comparisons are shown in Table 1.

TABLE 1

| | Comparison A 28 French (9.33 mm) | | | Comparison B 24 French (8 mm) | | | Comparison C 20 French (6.66 mm) | | |
|---|---|---|---|---|---|---|---|---|---|
| | Y | SD | N | Y | SD | N | Y | SD | N |
| DLP cannulas | 4.117 | 0.076 | 3 | 3.317 | 0.076 | 3 | 1.733 | 0.153 | 3 |
| Biomedicus cannulas | 3.983 | 0.046 | 3 | 3.930 | 0.036 | 3 | 2.670 | 0.070 | 3 |
| Chest tube | 3.603 | 0.055 | 3 | 2.947 | 0.117 | 3 | 2.210 | 0.046 | 3 |
| High performance cannulas | 5.350 | 0.132 | 3 | 5.217 | 0.076 | 3 | 4.173 | 0.087 | 3 |

The results depicted in Table 1 demonstrate the flow rate of fluids (Y) in L/min through each of the cannulas tested. The results also show the standard deviation (SD) and number tested (N) for each cannula. For all tested, clinically-relevant cannula diameters (i.e., 28 French, 24 French, and 20 French), the high performance cannulas described herein provided the best flow rate results. The flow rate of fluids through the high performance cannulas was 33-60% higher than the flow rate through the other commonly used, commercially available cannulas. Specifically, for the 20 French outflow vessel, the flow rate with the high performance cannula was superior to the flow rate for the best 28 French cannula (4.117 L/min vs. 4.173 L/min).

Thus, these results demonstrated that the high performance cannulas according to the instant invention are superior to the cannulas commonly used by those skilled in the art. These results provided proof of the principle that the flow rate usually generated with a 28 French cannula can also be provided by a high performance cannula requiring only a 20 French hole. The results of these in vivo comparisons are also shown in FIG. 12.

Example 2

Use of High Performance Cannulas

In order to prepare the high performance cannula 6 for use, a mandrel 7 (as shown, for example, in FIG. 3A) is introduced into the cannula 6. Next the cannula 6 is stretched over the mandrel 7 in order to reduce its diameter. Once the cannula 6 is fully in its low profile conformation, it will have a minimal outer diameter.

The vessel to be cannulated is then punctured with the sharp hollow needle. A J-tip guidewire 8 is then introduced into the vessel. Proper positioning of the guidewire is checked by ultrasound, fluoroscopy, or any other suitable means. While keeping the guidewire in place in situ, the needle is then removed from the vessel.

To achieve vessel orifice (e.g., access aperture) dilation, a small (e.g., No. 1) dilator is placed over the guidewire 8 and then removed, while the guidewire 8 remains in place. The access aperture can be redilated using an intermediate (No. 2) dilator that is inserted and removed. Finally, the largest dilator (No. 3) is inserted and removed.

While insuring that the guidewire 8 remains in the proper position, the fully stretched (e.g., low profile conformation) and locked high performance cannula 6 is loaded onto the guidewire 8. This is accomplished by passing the guidewire 8 through the central hole 9 at the tip 10 of the cannula 6 and through the central hole at the tip of the mandrel 7. The cannula 6 is inserted over the wire through the predilated hole in the vessel at the target site.

Once the mandrel 7 is unlocked, the cannula 6 can be pulled back at any time. However, for further advancement, reloading of the cannula 6 onto the mandrel 7 may be necessary. After the mandrel 7 is unlocked, the high performance cannula 6 will expand in situ. Prior to complete removal of the mandrel 7, the position of the cannula 6 should be checked and monitored.

Once an adequate cannula position is reached, the high performance cannula 6 may be secured and the mandrel 7 removed. Finally, the secured high performance cannula 6 can be connected to a line. A mandrel 7 may be used for repositioning, as necessary.

Example 3

Manufacture of High Performance Cannulas

The manufacture of the high performance cannulas may include some or all of the following steps: (a) defining the diameter and length needed; (b) selecting the appropriate materials; (c) preparing the cannula 6; (d) preparing the mandrel 7; and (e) preparing a locking mechanism 12. Additionally, those skilled in the relevant arts will recognize that the high performance cannulas of the invention may also be made by any other methods or processes known in the art.

A variety of parameters influence and define the optimal diameter and length configuration of the high performance cannulas of the invention. These parameters include target flow, target vessel diameter, target vessel length, target vessel access diameter, target vessel access length, desired covered cannula 6 length proximal to the point of insertion, and/or the desired connector. In one embodiment the cannula 6 can be approximately ⅜" in diameter and 50-70 cm in length, depending on the particular application. Determination of the appropriate diameter and length is within the routine skill of those in the art.

Suitable materials for manufacturing the high performance cannulas can be categorized as cannula size-independent materials and cannula size-dependent materials. Size-independent materials may include, but are not limited to, medical grade polyurethanes (used for potting the cannula tip 10), medical grade silicones (used for covering the portion of the cannula 6 close to the connector 11), and medical grade plastic separating agents. The cannula lumen 5 may contain a spacer that functions to maintain a hole for the guidewire 8 in the potted cannula tip 10.

Cannula size-dependent materials include the interlaced self-expanding wires and/or a plurality of flexible filaments that comprise the cannula body 4. The wires can be made of, for example, a medical grade stainless steel coated with a plastic. Alternatively, an elastic honeycomb structure, a grid, lasercut nitinol, or a plastic scaffold may be used. Other cannula size-dependent materials include molds for potting the cannula tip 10, the connector 11, the mandrel 7, and the locking mechanism 12.

The high performance cannulas 6 of the invention can be made with additional working length at both ends of the final cannula 6 dimensions. The interlaced wire bundle at the distal end 3 of the cannula 6 is tied together to a minimal diameter after the insertion of a central spacer wire, which has been treated with a separate form of the potting material. Any excess length can then be removed.

Using a mold prepared with a separating agent, the cannula tip 10 is positioned within the mold. A polyurethane used for potting is mixed, centrifuged, and potted on the cannula tip 10. Following polymerization and unmolding, the spacer is removed, thereby providing a path for the guidewire 8. The tip may be potted using a photoactivated epoxy. Finally, the cannula tip 10 is cut and polished.

Next, the proximal end 1 of the cannula 6 can be coated. Using positioning tools, a partial length dip coating of the proximal end 1 is performed. This dip coating can be a medical grade silicone or any other suitable coating. This coating is then polymerized, and several additional layers can be added. Finally, the proximal end 1 of the cannula 6 can be mounted with an appropriate connector 11. Alternatively (or additionally), various segments of the cannula may be coated (i.e., in an alternating fashion).

In order to prepare the mandrel 7, an adequate diameter of Teflon (or any other flexible (i.e., plastic) rod having a conical tip and a central lumen for the guidewire 8, is used. The length of this rod is then adapted for the length of the high performance cannula 6 to be used.

Figure 12B:
FIG. 12B illustrates one view of a locking mechanism for use with the high performance cannulas of the invention.
Figure 12C:
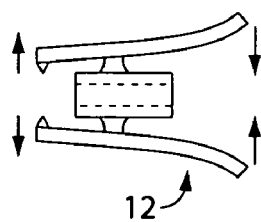
FIG. 12C illustrates another view of a locking mechanism for use with the high performance cannulas of the invention.

Finally, the locking mechanism 12 is made by selecting an adequate cap with a locking mechanism that is assembled with the cannula 6. Care should be taken to select a locking mechanism 12 of proper length for the selected high performance cannula 6. An example of an appropriate locking mechanism 12 is illustrated in FIGS. 12A-12C. Alternatively, the connector is capped with a plug. When connecting the cannula to a device such as a perfusion machine, a connecting sleeve is used in place of the connector and locking mechanism. A sleeve capable of coupling the cannula to the machine is selected and placed over the proximal end of the cannula.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed is:

1. A dual lumen cannula adapted for insertion at a point of insertion for use in peritoneal dialysis, hemodialysis or hemofiltration, the cannula comprising:
   a first cannula body having a proximal end, a distal end, and a first lumen extending between the proximal and distal ends, and
   a second cannula body having a proximal end, a distal end, and a second lumen extending between the proximal and distal ends, wherein,
      the lumen of the first and second cannula bodies each include a corresponding diameter,
      the diameter of the first and second lumen may be varied, and
      at least one of the first and second distal ends further comprise a tip,
      wherein the tip is removable or eccentrically located;
      wherein at least one of the cannula bodies comprises a plurality of flexible filaments;
   at least one mechanism that, upon actuation, serves to alter the conformation of the first cannula body and/or the second cannula body, between a normal profile conformation and a low profile conformation; wherein,
      the lumen diameters of at least one of the first and second cannula bodies distal to the point of insertion are expandable up to the diameter of a surrounding vessel, environment, or to the maximum lumen diameter.

2. A method for using the dual lumen cannula of claim 1 in a non-medical context, the method comprising:
   placing the cannula in its low profile conformation;
   inserting the cannula into an object to be cannulated selected from the group consisting of tubing, a container, a fluid-filled container, a powder-filled container, and a gas filled container; and
   returning the cannula to its normal profile conformation, wherein in the normal profile conformation, the cannula expands distal to the point of insertion up to the diameter of the object or up to the maximum lumen diameter.

3. The dual lumen cannula of claim 1, wherein said filaments comprise one or more materials selected from the group consisting of metals, shape-memory metals, alloys, plastics, textile fibers, synthetic fibers, and combinations thereof.

4. The dual lumen cannula of claim 1, wherein the at least one mechanism is selected from the group consisting of a mandrel, an electric motor, a change in pressurization, a wrapping string, a balloon and a sheath.

5. The dual lumen cannula of claim 1, wherein the first and second cannula bodies are positioned coaxially.

6. The dual lumen cannula of claim 5, wherein the respective cannula body comprising an inner cannula in the coaxial arrangement comprises a soft, collapsible and flexible material.

7. The dual lumen cannula of claim 1, wherein the first and second cannula bodies are positioned adjacently.

8. The dual lumen cannula of claim 1, wherein when the dual lumen cannula is in use, the normal profile conformation is characterized by the first and second cannula bodies having a lumen diameter at the point of insertion which is smaller than the lumen diameter both proximal and distal to the point of insertion.

9. The dual lumen cannula of claim 1, wherein the low profile conformation is characterized by the first and second cannula bodies having a lumen diameter at the point of insertion that is greater than the lumen diameter distal to the point of insertion.

10. A method of using the cannula of claim 1, the method comprising:
    placing the cannula in its low profile conformation;
    inserting the cannula; and
    returning the cannula to its normal profile conformation, wherein in the normal profile conformation, the cannula expands distal to the point of insertion.

11. A method of using the cannula of claim 1, the method comprising:
    activating the at least one mechanism;
    inserting the cannula; and
    deactivating the at least one mechanism, thereby allowing the cannula to expand distal to the point of insertion.

12. A dual lumen cannula adapted for insertion at a point of insertion for use in peritoneal dialysis, hemodialysis or hemofiltration, the cannula comprising:
    only two cannula bodies including
        a first cannula body having a proximal end, a distal end, and a first lumen extending between the proximal and distal ends, and
        a second cannula body having a proximal end, a distal end, and a second lumen extending between the proximal and distal ends, wherein,
            the lumen of the first and second cannula bodies each include a corresponding diameter,
            the diameter of the first and second lumen may be varied, and
            at least one of the first and second distal ends further comprise a tip, wherein the tip is removable or eccentrically located;
            wherein at least one of the cannula bodies comprises a plurality of flexible filaments;
    at least one mechanism that, upon actuation, serves to alter the conformation of the first cannula body and/or the second cannula body, between a normal profile conformation and a low profile conformation; wherein,
        the lumen diameters of at least one of the first and second cannula bodies distal to the point of insertion are expandable up to the diameter of a surrounding vessel, environment, or to the maximum lumen diameter.

* * * * *